US006190381B1

(12) United States Patent
Olsen et al.

(10) Patent No.: US 6,190,381 B1
(45) Date of Patent: *Feb. 20, 2001

(54) METHODS FOR TISSUE RESECTION, ABLATION AND ASPIRATION

(75) Inventors: Phillip M. Olsen, Sunnyvale; Maria B. Ellsberry, Fremont; David C. Hovda, Mountain View; Hira V. Thapliyal, Los Altos, all of CA (US); Philip E. Eggers, Dublin, OH (US)

(73) Assignee: ArthroCare Corporation, Sunnyvale, CA (US)

( * ) Notice: Under 35 U.S.C. 154(b), the term of this patent shall be extended for 0 days.

This patent is subject to a terminal disclaimer.

(21) Appl. No.: 09/010,382

(22) Filed: Jan. 21, 1998

Related U.S. Application Data

(60) Continuation-in-part of application No. 08/795,686, filed on Feb. 5, 1997, now Pat. No. 5,871,469, which is a division of application No. 08/561,958, filed on Nov. 22, 1995, now Pat. No. 5,697,882, which is a continuation-in-part of application No. 08/990,374, filed on Dec. 15, 1997, now Pat. No. 6,109,268, which is a continuation-in-part of application No. 08/485,219, filed on Jun. 7, 1995, now Pat. No. 5,697,281
(60) Provisional application No. 60/062,996, filed on Oct. 23, 1997.

(51) Int. Cl.⁷ .................................................. A61B 18/14
(52) U.S. Cl. .............................. 606/32; 606/41; 606/45; 606/46; 604/114; 604/35; 607/105; 607/113
(58) Field of Search ....................... 606/41, 45, 46, 606/48–50, 32; 604/114, 35; 607/99, 105, 113

(56) References Cited

U.S. PATENT DOCUMENTS

| 2,050,904 | 8/1936 | Trice . | |
| 2,275,167 | * 3/1942 | Bierman | 606/42 |
| 4,033,351 | 7/1977 | Hetzel | 128/303 |
| 4,040,426 | 8/1977 | Morrison, Jr. | 128/303 |
| 4,043,342 | 8/1977 | Morrison, Jr. | 128/303 |

(List continued on next page.)

FOREIGN PATENT DOCUMENTS

| 0 703 461 | 3/1996 | (EP) | G01R/27/02 |
| 0 740 926 A2 | 11/1996 | (EP) | A61B/17/39 |
| 0 754 437 | 1/1997 | (EP) | A61B/17/39 |
| 2 308 979 | 7/1997 | (GB) | A61B/17/36 |
| 2 308 980 | 7/1997 | (GB) | A61B/17/36 |
| 2 308 981 | 7/1997 | (GB) | A61B/17/36 |
| 2 327 350 | 1/1999 | (GB) | A61B/17/39 |
| 2 327 351 | 1/1999 | (GB) | A61B/17/39 |
| 2 327 352 | 1/1999 | (GB) | A61B/17/39 |

(List continued on next page.)

OTHER PUBLICATIONS

Pearce, John A. (1986) *Electrosurgery*, pp. 17, 69–75, 87, John Wiley & Sons, New York.

V. E. Elsasser et al. *Acta Medicotechnica* vol. 24, No. 4, pp. 129–134 (1976).

P. C. Nardella (1989) *SPIE* 1068:42–49 Radio Frequency Energy and Impedance Feedback.

(List continued on next page.)

*Primary Examiner*—Lee Cohen
(74) *Attorney, Agent, or Firm*—John T. Raffle

(57) ABSTRACT

The present invention provides systems and methods for selectively applying electrical energy to a target location within or on a patient's body. In particular, methods and apparatus are provided for resecting, cutting, partially ablating, aspirating or otherwise removing tissue from a target site, and ablating the tissue in situ. The systems and methods of the present invention are particularly useful for ablation and hemostasis of tissue in sinus surgery (e.g., chronic sinusitis and/or removal of polypectomies) and for resecting and ablating soft tissue structures, such as the meniscus and synovial tissue within a joint.

16 Claims, 17 Drawing Sheets

U.S. PATENT DOCUMENTS

| | | | |
|---|---|---|---|
| 4,116,198 | 9/1978 | Roos | 128/303 |
| 4,184,492 | 1/1980 | Meinke et al. | 128/303 |
| 4,202,337 | 5/1980 | Hren et al. | 128/303 |
| 4,228,800 | 10/1980 | Degler, Jr. et al. | 128/303 |
| 4,232,676 | 11/1980 | Herczog | 128/303 |
| 4,248,231 | 2/1981 | Herczog et al. | 128/303 |
| 4,326,529 | 4/1982 | Doss et al. | 128/303 |
| 4,381,007 | 4/1983 | Doss | 128/303 |
| 4,476,862 | 10/1984 | Pao | 128/303 |
| 4,532,924 | 8/1985 | Auth et al. | 128/303 |
| 4,548,207 | 10/1985 | Reimels | 128/303 |
| 4,567,890 | 2/1986 | Ohta et al. | 128/303 |
| 4,593,691 | 6/1986 | Lindstrom et al. | 128/303 |
| 4,674,499 | 6/1987 | Pao | 128/303 |
| 4,682,596 | 7/1987 | Bales et al. | 128/303 |
| 4,706,667 | 11/1987 | Roos | 128/303 |
| 4,709,698 | 12/1987 | Johnston et al. | 128/303 |
| 4,727,874 | 3/1988 | Bowers et al. | 128/303 |
| 4,765,331 | 8/1988 | Petruzzi et al. | 128/303 |
| 4,823,791 | 4/1989 | D'Amelio et al. | 123/303 |
| 4,832,048 * | 5/1989 | Cohen | 606/41 |
| 4,860,752 | 8/1989 | Turner | 128/422 |
| 4,931,047 | 6/1990 | Broadwin et al. | 604/22 |
| 4,936,301 | 6/1990 | Rexroth et al. | 606/45 |
| 4,943,290 | 7/1990 | Rexroth et al. | 606/45 |
| 4,955,377 | 9/1990 | Lennox et al. | 128/401 |
| 4,967,765 | 11/1990 | Turner et al. | 128/785 |
| 4,976,711 | 12/1990 | Parins et al. | 606/48 |
| 4,979,948 | 12/1990 | Geddes et al. | 606/33 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,035,696 | 7/1991 | Rydell | 606/47 |
| 5,057,105 | 10/1991 | Malone et al. | 606/28 |
| 5,057,106 | 10/1991 | Kasevich et al. | 606/33 |
| 5,078,717 | 1/1992 | Parins et al. | 606/48 |
| 5,080,660 | 1/1992 | Buelna | 606/45 |
| 5,083,565 | 1/1992 | Parins | 128/642 |
| 5,098,431 | 3/1992 | Rydell | 606/48 |
| 5,108,391 | 4/1992 | Flachenecker et al. | 606/38 |
| 5,112,330 | 5/1992 | Nishigaki et al. | 606/46 |
| 5,122,138 | 6/1992 | Manwaring | 606/46 |
| 5,125,928 | 6/1992 | Parins et al. | 606/48 |
| 5,178,620 | 1/1993 | Eggers et al. | 606/41 |
| 5,190,517 | 3/1993 | Zieve et al. | 604/22 |
| 5,192,280 | 3/1993 | Parins | 606/48 |
| 5,195,959 | 3/1993 | Smith | 604/34 |
| 5,197,963 | 3/1993 | Parins | 606/46 |
| 5,217,457 | 6/1993 | Delahuerga et al. | 606/42 |
| 5,249,585 | 10/1993 | Turner et al. | 607/99 |
| 5,267,994 | 12/1993 | Gentelia et al. | 606/15 |
| 5,267,997 | 12/1993 | Farin et al. | 606/38 |
| 5,273,524 | 12/1993 | Fox et al. | 604/21 |
| 5,277,201 | 1/1994 | Stern | 607/98 |
| 5,277,696 * | 1/1994 | Hagen | 606/41 |
| 5,281,216 | 1/1994 | Klicek | 606/42 |
| 5,281,218 | 1/1994 | Imran | 606/41 |
| 5,290,282 | 3/1994 | Casscells | 606/29 |
| 5,300,069 | 4/1994 | Hunsberger et al. | 606/37 |
| 5,312,400 | 5/1994 | Bales et al. | 606/41 |
| 5,314,406 | 5/1994 | Arias et al. | 604/21 |
| 5,318,563 | 6/1994 | Malis et al. | 606/38 |
| 5,324,254 | 6/1994 | Phillips | 604/21 |
| 5,330,470 | 7/1994 | Hagen | 606/42 |
| 5,334,140 | 8/1994 | Philips | 604/35 |
| 5,334,183 | 8/1994 | Wuchinich | 606/46 |
| 5,336,220 | 8/1994 | Ryan et al. | 604/22 |
| 5,342,357 | 8/1994 | Nardella | 606/40 |
| 5,366,443 | 11/1994 | Eggers et al. | 604/114 |
| 5,370,675 | 12/1994 | Edwards et al. | 607/101 |
| 5,380,277 | 1/1995 | Phillips | 604/33 |
| 5,383,876 | 1/1995 | Nardella | 606/49 |
| 5,383,917 | 1/1995 | Desai et al. | 607/702 |
| 5,395,312 | 3/1995 | Desai | 604/22 |
| 5,417,687 | 5/1995 | Nardella et al. | 606/32 |
| 5,419,767 | 5/1995 | Eggers et al. | 604/114 |
| 5,441,499 | 8/1995 | Fritzsch | 606/45 |
| 5,454,809 | 10/1995 | Janssen | 606/41 |
| 5,496,312 | 3/1996 | Klicek | 606/34 |
| 5,514,130 | 5/1996 | Baker | 606/41 |
| 5,556,397 | 9/1996 | Long et al. | 606/48 |
| 5,569,242 | 10/1996 | Lax et al. | 606/42 |
| 5,584,872 | 12/1996 | LaFontaine et al. | 607/117 |
| 5,609,151 | 3/1997 | Mulier et al. | 128/642 |
| 5,647,869 | 7/1997 | Goble et al. | 606/37 |
| 5,662,680 | 9/1997 | Desai | 606/210 |
| 5,676,693 | 10/1997 | LaFontaine et al. | 607/116 |
| 5,681,282 | 10/1997 | Eggers et al. | 604/114 |
| 5,683,366 | 11/1997 | Eggers et al. | 604/114 |
| 5,697,281 | 12/1997 | Eggers et al. | 604/114 |
| 5,697,536 | 12/1997 | Eggers et al. | 604/114 |
| 5,697,882 * | 12/1997 | Eggers et al. | 604/114 |
| 5,697,909 | 12/1997 | Eggers et al. | 604/114 |
| 5,700,262 | 12/1997 | Acosta et al. | 606/48 |
| 5,725,524 | 3/1998 | Mulier et al. | 606/41 |
| 5,743,870 * | 4/1998 | Edwards | 604/22 |
| 5,749,869 | 5/1998 | Lindenmeier et al. | 606/34 |
| 5,766,153 | 6/1998 | Eggers et al. | 604/114 |
| 5,800,429 * | 9/1998 | Edwards | 606/41 |
| 5,800,431 | 9/1998 | Brown | 606/42 |
| 5,807,395 | 9/1998 | Mulier et al. | 606/41 |
| 5,810,764 | 9/1998 | Eggers et al. | 604/23 |
| 5,810,809 | 9/1998 | Rydell | 606/49 |
| 5,843,019 | 12/1998 | Eggers et al. | 604/22 |
| 5,871,469 | 2/1999 | Eggers et al. | 604/114 |
| 5,885,277 | 3/1999 | Korth | 606/35 |
| 5,888,198 | 3/1999 | Eggers et al. | 604/114 |
| 5,891,095 | 4/1999 | Eggers et al. | 604/114 |
| 5,897,553 | 4/1999 | Mulier | 606/41 |
| 5,902,272 | 5/1999 | Eggers et al. | 604/114 |
| 5,944,715 * | 8/1999 | Goble et al. | 606/41 |
| 6,004,319 | 12/1999 | Goble et al. | 606/48 |
| 6,013,076 | 1/2000 | Goble et al. | 606/41 |
| 6,015,406 | 1/2000 | Goble et al. | 606/41 |
| 6,027,501 | 2/2000 | Goble et al. | 606/41 |
| 6,039,734 | 3/2000 | Goble et al. | 606/41 |
| 6,056,746 | 5/2000 | Goble et al. | 606/48 |
| 6,066,134 | 5/2000 | Eggers et al. | 606/32 |
| 6,068,628 | 5/2000 | Fanton et al. | 606/41 |
| 6,074,386 | 6/2000 | Goble et al. | 606/34 |
| 6,090,106 | 7/2000 | Goble et al. | 606/41 |
| 6,093,186 | 7/2000 | Goble et al. | 606/34 |

FOREIGN PATENT DOCUMENTS

| | | | |
|---|---|---|---|
| 57-57802 | 4/1982 | (JP) | A61B/1/00 |
| 57-117843 | 7/1982 | (JP) | A61B/17/39 |
| WO 90/07303 | 7/1990 | (WO) | A61B/17/39 |
| 92/21278 | 12/1992 | (WO) | A61B/5/04 |
| WO 93/13816 | 7/1993 | (WO) | A61B/17/36 |
| 93/20747 | 10/1993 | (WO) | A61B/5/00 |
| WO 94/04220 | 3/1994 | (WO) | A61N/1/06 |
| 94/08654 | 4/1994 | (WO) | A61M/37/00 |
| WO95/34259 | 12/1995 | (WO) | A61F/5/48 |
| 96/00042 | 1/1996 | (WO) | A61B/17/39 |
| 97/00646 | 1/1997 | (WO) | A61B/17/39 |
| 97/00647 | 1/1997 | (WO) | A61B/17/39 |
| 97/24073 | 7/1997 | (WO) | A61B/17/39 |
| 97/24993 | 7/1997 | (WO) | A61B/17/39 |
| 97/24994 | 7/1997 | (WO) | A61B/17/39 |
| 97/48345 | 12/1997 | (WO) | A61B/17/39 |
| 97/48346 | 12/1997 | (WO) | A61B/17/39 |

| | | | |
|---|---|---|---|
| 98/07468 | 2/1998 | (WO) | A61N/1/40 |
| 98/27879 | 7/1998 | (WO) | A61B/17/36 |
| 98/27880 | 7/1998 | (WO) | A61B/17/39 |
| 99/51155 | 10/1999 | (WO) | A61B/17/36 |
| 99/51158 | 10/1999 | (WO) | A61B/17/39 |

OTHER PUBLICATIONS

Rand et al. (1985) *J. Arthro. Surg.* 1:242–246 Effect of Electrocautery on Fresh Human Articular Cartilage.

Buchelt, M. et al., "Excimer Laser Ablation of Fibrocartilage: An In Vitro and In Vivo Study," (1991) Lasers in Surgery and Medicine 11:271–279.

Costello, A. J. et al. "Nd:YAG Laser Ablation of the Prostate as a Treatment of Benign Prostatic Hypertrophy," (1992) Lasers in Surger and Medicine 12:121–124.

J. W. Ramsey et al. *Urological Research* vol. 13, pp. 99–102 (1985).

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

Kramolowsky et al. *J. of Urology* vol. 143, pp. 275–277 (1990).

Kramolowsky et al. *J. of Urology* vol. 146, pp. 669–674 (1991).

Slager et al. *Z. Kardiol.* 76:Suppl. 6, 67–71 (1987).

Slager et al. *JACC* 5(6) :1382–6 (1985).

* cited by examiner

METHODS FOR TISSUE RESECTION, ABLATION AND ASPIRATION

RELATED APPLICATIONS

The present invention is a continuation-in-part of U.S. application Ser. No. 08/795,686, filed Feb. 5, 1997 (now U.S. Pat. No. 5,871,469), which is a divisional application of U.S. application Ser. No. 08/561,958, filed Nov. 22, 1995 (now U.S. Pat. No. 5,697,882). This application is also a continuation-in-part of U.S. patent application Ser. No. 08/990,374 filed on Dec. 15, 1997 now U.S. Pat. No. 6,109,268, which is a continuation-in-part of application Ser. No. 08/485,219, filed on Jun. 7, 1995, now U.S. Pat. No. 5,697,281, the complete disclosure of which is incorporated herein by reference for all purposes. The present invention also derives priority from Provisional patent application No. 60/062,996, filed on Oct. 23, 1997.

The present invention is related to commonly assigned co-pending Provisional patent application No. 60/062,997, filed on Oct. 23, 1997, non-provisional U.S. patent applications No. 08/977,845, filed on Nov. 25, 1997, filed on Oct. 2, 1997, U.S. application Ser. No. 08/753,227, filed on Nov. 22, 1996, U.S. application Ser. No. 08/687,792, filed on Jul. 18, 1996, and PCT International Application, U.S. National Phase Serial No. PCT/US94/05168, filed on May 10, 1994, which was a continuation-in-part of application Ser. No. 08/059,681, filed on May 10, 1993, which was a continuation-in-part of application Ser. No. 07/958,977, filed on Oct. 9, 1992 which was a continuation-in-part of application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to resect, coagulate, ablate and aspirate cartilage, bone and tissue, such as sinus tissue, or meniscus and synovial tissue in a joint.

Conventional electrosurgical methods are widely used since they generally reduce patient bleeding associated with tissue cutting operations and improve the surgeon's visibility. These electrosurgical devices and procedures, however, suffer from a number of disadvantages. For example, monopolar electrosurgery methods generally direct electric current along a defined path from the exposed or active electrode through the patient's body to the return electrode, which is externally attached to a suitable location on the patient's skin. In addition, since the defined path through the patient's body has a relatively high electrical impedance, large voltage differences must typically be applied between the active and return electrodes to generate a current suitable for cutting or coagulation of the target tissue. This current, however, may inadvertently flow along localized pathways in the body having less impedance than the defined electrical path. This situation will substantially increase the current flowing through these paths, possibly causing damage to or destroying tissue along and surrounding this pathway.

Bipolar electrosurgical devices have an inherent advantage over monopolar devices because the return current path does not flow through the patient beyond the immediate site of application of the bipolar electrodes. In bipolar devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue.

Another limitation of conventional bipolar and monopolar electrosurgery devices is that they are not suitable for the precise removal (i.e., ablation) or tissue. In addition, conventional electrosurgical methods are generally not that effective with certain types of tissue, and in certain types of environments within the body. For example, loose or elastic connective tissue, such as the synovial tissue in joints, is extremely difficult (if not impossible) to remove with conventional electrosurgical instruments because the flexible tissue tends to move away from the instrument when it is brought against this tissue. Since conventional techniques rely mainly on conducting current through the tissue, they are not effective when the instrument cannot be brought adjacent to or in contact with the elastic tissue for a long enough period of time to energize the electrode and conduct current through the tissue.

The use of electrosurgical procedures (both monopolar and bipolar) in electrically conductive environments can be further problematic. For example, many arthroscopic procedures require flushing of the region to be treated with isotonic saline, both to maintain an isotonic environment and to keep the field of view clear. However, the presence of saline, which is a highly conductive electrolyte, can cause shorting of the active electrode(s) in conventional monopolar and bipolar electrosurgery. Such shorting causes unnecessary heating in the treatment environment and can further cause non-specific tissue destruction.

Conventional electrosurgical cutting or resecting devices also tend to leave the operating field cluttered with tissue fragments that have been removed or resected from the target tissue. These tissue fragments make visualization of the surgical site extremely difficult. Removing these tissue fragments can also be problematic. Similar to synovial tissue, it is difficult to maintain contact with tissue fragments long enough to ablate the tissue fragments in situ with conventional devices. To solve this problem, the surgical site is periodically or continuously aspirated during the procedure. However, the tissue fragments often clog the aspiration lumen of the suction instrument, forcing the surgeon to remove the instrument to clear the aspiration lumen or to introduce another suction instrument, which increases the length and complexity of the procedure.

SUMMARY OF THE INVENTION

The present invention provides systems, apparatus and methods for selectively applying electrical energy to structures within or on the surface of a patient's body. In particular, methods and apparatus are provided for resecting, cutting, partially ablating, aspirating or otherwise removing tissue from a target site, and ablating the tissue in situ. The systems and methods of the present invention are particularly useful for ablation and hemostasis of tissue in sinus surgery (e.g., chronic sinusitis and/or removal of polypectomies) and for resecting and ablating soft tissue structures, such as the meniscus and synovial tissue within a joint.

In one aspect of the invention, a method comprises introducing a distal end of an electrosurgical instrument, such as a probe or a catheter, to the target site, and aspirating tissue from the target site through one or more aspiration lumen(s) in the instrument. High frequency voltage is applied between one or more aspiration electrode(s) coupled to the aspiration lumen(s) and one or more return electrode(s) so that an electric current flows therebetween. The high frequency voltage is sufficient to remove or ablate at least a portion of the tissue before the tissue passes into the aspiration lumen(s). This partial or total ablation reduces the size of the aspirated tissue fragments to inhibit clogging of the aspiration lumen.

The aspiration electrode(s) are usually located near or at the distal opening of the aspiration lumen so that tissue can be partially ablated before it becomes clogged in the aspiration lumen. In some embodiments, the aspiration electrodes(s) are adjacent to the distal opening, or they may extend across the distal opening of the lumen. The latter configuration has the advantage of ensuring that the tissue passing through the aspiration lumen will contact the aspiration electrode(s). In other embodiments, the aspiration electrode(s) may be positioned within the aspiration lumen just proximal of the distal opening. The aspiration electrode(s) may comprise a loop, a coiled structure, a hook, or any other geometry suitable for ablating the aspirated tissue. In an exemplary embodiment, the electrosurgical probe comprises a pair of loop electrodes disposed across the distal end of the suction lumen.

The electrosurgical probe will preferably also include one or more ablation electrode(s) for removing or ablating tissue at the target site. Typically, the ablation electrode(s) are different from the aspiration electrode(s), although the same electrodes may serve both functions. In an exemplary embodiment, the probe includes a plurality of electrically isolated electrode terminals surrounding the distal opening of the aspiration lumen. High frequency voltage is applied between the electrode terminals and a return electrode to ablate tissue at the target site. During the procedure, fluid and/or non-ablated tissue fragments are aspirated from the target site to improve visualization. Preferably, one or more of the electrode terminals are loop electrodes that extend across the distal opening of the suction lumen to ablate, or at least reduce the volume of, the tissue fragments, thereby inhibiting clogging of the lumen. The aspiration or loop electrodes may be energized with the active electrode terminal(s), or they may be isolated from the electrode terminal(s) so that the surgeon may select which electrodes are activated during the procedure.

In some embodiments, the return electrode(s) comprises an annular electrode member on the probe itself, spaced proximally from the aspiration and ablation electrodes. In these embodiments, electrically conducting fluid, such as isotonic saline, is preferably used to generate a current flow path between the aspiration electrode(s) and the return electrode(s). High frequency voltage is then applied between the electrode terminal(s) and the return electrode(s) through the current flow path created by the electrically conducting fluid. Depending on the procedure, the electrically conductive fluid may be delivered to the target site through, for example, a fluid lumen in the probe or a separate instrument, or the fluid may already be present at the target site, as is the case in many arthroscopic procedures.

In a specific configuration, the tissue is removed by molecular dissociation or disintegration processes. In these embodiments, the high frequency voltage applied to the electrode terminal(s) is sufficient to vaporize an electrically conductive fluid (e.g., gel or saline) between the electrode terminal(s) and the tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,683,366, the complete disclosure of which is incorporated herein by reference.

The present invention offers a number of advantages over conventional electrosurgery, microdebrider and laser techniques for removing soft tissue in arthroscopic, sinus or other surgical procedures. The ability to precisely control the volumetric removal of tissue results in a field of tissue ablation or removal that is very defined, consistent and predictable. The shallow depth of tissue heating also helps to minimize or completely eliminate damage to healthy tissue structures, cartilage, bone and/or cranial nerves that are often adjacent the target sinus tissue. In addition, small blood vessels at the target site are simultaneously cauterized and sealed as the tissue is removed to continuously maintain hemostasis during the procedure. This increases the surgeon's field of view, and shortens the length of the procedure. Moreover, since the present invention allows for the use of electrically conductive fluid (contrary to prior art bipolar and monopolar electrosurgery techniques), isotonic saline may be used during the procedure. Saline is the preferred medium for irrigation because it has the same concentration as the body's fluids and, therefore, is not absorbed into the body as much as other fluids.

In another aspect of the invention, a method comprises positioning one or more resection electrode(s) adjacent the target tissue, and applying high frequency voltage between the resection electrode(s) and one or more return electrode(s) to resect a tissue fragment away from the tissue structure. High frequency voltage is then applied between one or more ablation electrode(s) and one or more return electrode(s) to ablate the tissue fragment in situ. The ablation electrode(s) may be the same electrodes as the resection electrode(s), or they may be different electrodes spaced from the resection electrode(s). Removing the resected tissue fragments improves the surgeon's visibility of the target site, and eliminates the potential of this tissue from remaining in the body after the surgical procedure.

Alternatively, the loop electrode(s) may be used to ablate (i.e., volumetrically remove) tissue directly at the target site using the mechanisms described above. Applicant has found that the loop electrode(s) have a larger surface area exposed to electrically conductive fluid than the active electrode terminals described above. Therefore, the loop electrode(s) typically provide a stronger plasma layer, which leads to faster tissue ablation rates for the same applied voltage levels. In addition, the loop electrode configuration provides a relative smooth, uniform cutting effect across the tissue.

In a specific configuration, an electrosurgical probe according to the invention comprises a shaft having an electrically insulating support at or near the distal end of the shaft. The instrument further includes one or more loop electrode(s) extending from the insulating support for resection or ablation of tissue, and one or more electrode terminal(s) for ablation of tissue fragments that have been resected by the loop electrode(s.) The electrode terminal(s) may comprise an array of electrode terminals or a single electrode at the distal end of the electrosurgical probe. In a specific embodiment, one or more return electrode(s) are positioned in contact with electrically conducting fluid to provide a current flow path from the electrode terminal(s), through the electrically conducting fluid, to the return electrode(s).

In yet another aspect of the invention, a method comprises positioning one or more active electrode(s) at the target site within a patient's body and applying a suction force to a tissue structure to draw the tissue structure to the active electrode(s). High frequency voltage is then applied between the active electrode(s) and one or more return electrode(s) to ablate the tissue structure. Typically, the tissue structure comprises a flexible or elastic connective tissue, such as synovial tissue. This type of tissue is typically difficult to remove with conventional mechanical and electrosurgery techniques because the tissue moves away from the instrument. The present invention, by contrast, draws the elastic tissue towards the active electrodes, and then ablates this tissue with the mechanisms described above

DESCRIPTION OF SPECIFIC EMBODIMENTS

Figure 1:
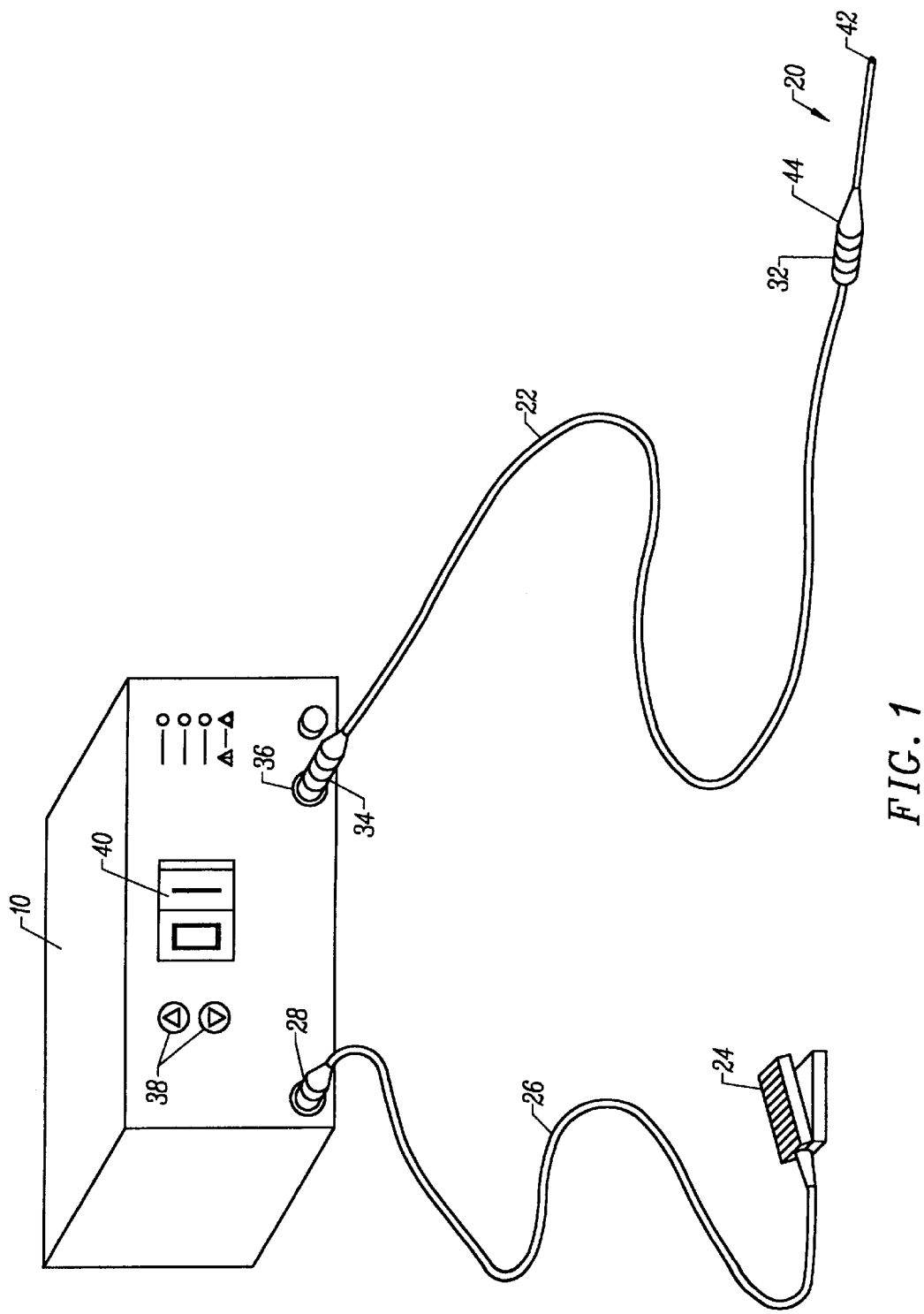
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body. The present invention is particularly useful in procedures where the tissue site is flooded or submerged with an electrically conducting fluid, such as arthroscopic surgery of the knee, shoulder, ankle, hip, elbow, hand or foot. In addition, tissues which may be treated by the system and method of the present invention include, but are not limited to, prostate tissue and leiomyomas (fibroids) located within the uterus, gingival tissues and mucosal tissues located in the mouth, tumors, scar tissue, myocardial tissue, collagenous tissue within the eye or epidermal and dermal tissues on the surface of the skin. Other procedures include laminectomy/disketomy procedures for treating herniated disks, decompressive laminectomy for stenosis in the lumbosacral and cervical spine, posterior lumbosacral and cervical spine fusions, treatment of scoliosis associated with vertebral disease, foraminotomies to remove the roof of the intervertebral foramina to relieve nerve root compression and anterior cervical and lumbar diskectomies. The present invention is also useful for resecting tissue within accessible sites of the body that are suitable for electrode loop resection, such as the resection of prostate tissue, leiomyomas (fibroids) located within the uterus and other diseased tissue within the body.

The present invention is also useful for procedures in the head and neck, such as the ear, mouth, pharynx, larynx, esophagus, nasal cavity and sinuses. These procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucus linings, polyps and/or neoplasms from the various anatomical sinuses of the skull, the turbinates and nasal passages, in the tonsil, adenoid, epi-glottic and supraglottic regions, and salivary glands, submucus resection of the nasal septum, excision of diseased tissue and the like. In other procedures, the present invention may be useful for collagen shrinkage, ablation and/or hemostasis in procedures for treating snoring and obstructive sleep apnea (e.g., soft palate, such as the uvula, or tongue/pharynx stiffening, and midline glossectomies), for gross tissue removal, such as tonsillectomies, adenoidectomies, tracheal stenosis and vocal cord polyps and lesions, or for the resection or ablation of facial tumors or tumors within the mouth and pharynx, such as glossectomies, laryngectomies, acoustic neuroma procedures and nasal ablation procedures. In addition, the present invention is useful for procedures within the ear, such as stapedotomies, tympanostomies or the like.

The present invention may also be useful for cosmetic and plastic surgery procedures in the head and neck. For example, the present invention is particularly useful for ablation and sculpting of cartilage tissue, such as the cartilage within the nose that is sculpted during rhinoplasty procedures. The present invention may also be employed for skin tissue removal and/or collagen shrinkage in the epidermis or dermis tissue in the head and neck, e.g., the removal of pigmentations, vascular lesions (e.g., leg veins), scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

For convenience, the remaining disclosure will be directed specifically to the resection and/or ablation of the meniscus and the synovial tissue within a joint during an arthroscopic procedure and to the ablation, resection and/or aspiration of sinus tissue during an endoscopic sinus surgery procedure, but it will be appreciated that the system and method can be applied equally well to procedures involving other tissues of the body, as well as to other procedures including open procedures, intravascular procedures, urology, laparoscopy, arthroscopy, thoracoscopy or other cardiac procedures, dermatology, orthopedics, gynecology, otorhinolaryngology, spinal and neurologic procedures, oncology and the like.

In the present invention, high frequency (RF) electrical energy is applied to one or more electrode terminals in the presence of electrically conductive fluid to remove and/or modify the structure of tissue structures. Depending on the specific procedure, the present invention may be used to: (1) volumetrically remove tissue, bone or cartilage (i.e., ablate or effect molecular dissociation of the tissue structure); (2) cut or resect tissue; (3) shrink or contract collagen connective tissue; and/or (4) coagulate severed blood vessels.

In one aspect of the invention, systems and methods are provided for the volumetric removal or ablation of tissue structures. In these procedures, a high frequency voltage difference is applied between one or more electrode terminal (s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a gas or liquid, such as isotonic saline, delivered to the target site, or a viscous fluid, such as a gel, that is located at the target site. In the latter embodiment, the electrode terminal(s) are submersed in the electrically conductive gel during the surgical procedure. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this cold ablation phenomena, termed Coblation, can be found in commonly assigned U.S. Pat. No. 5,683,366 the complete disclosure of which is incorporated herein by reference.

The present invention applies high frequency (RF) electrical energy in an electrically conducting fluid environment to remove (i.e., resect, cut or ablate) or contract a tissue structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate or contract with the electrode terminal(s). In other embodiments, the power supply is combined with the coagulation probe such that the coagulation electrode is used when the power supply is in the coagulation mode (low voltage), and the electrode terminal(s) are used when the power supply is in the ablation mode (higher voltage).

In the method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different probe may be pressed against the severed vessel. Once the vessel is adequately sealed, the surgeon activates a control (e.g., another foot pedal) to increase the voltage of the power supply back into the ablation mode.

The present invention is particularly useful for removing or ablating tissue around nerves, such as spinal or cranial nerves, e.g., the olfactory nerve on either side of the nasal cavity, the optic nerve within the optic and cranial canals, the palatine nerve within the nasal cavity, soft palate, uvula and tonsil, etc. One of the significant drawbacks with the prior art microdebriders and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or endoneurium, enclosing the bundles of nerve fibers to protect these nerve fibers. This protective tissue sheath typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more electrode terminal(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In one embodiment, the current limiting elements (discussed in detail above) are configured such that the electrode terminals will shut down or turn off when the electrical impedance reaches a threshold level. When this threshold level is set to the impedance of the fatty tissue surrounding nerves, the electrode terminals will shut off whenever they come in contact with, or in close proximity to, nerves. Meanwhile, the other electrode terminals, which are in contact with or in close proximity to nasal tissue, will continue to conduct electric current to the return electrode. This selective ablation or removal of lower impedance tissue in combination with the Coblation™ mechanism of the present invention allows the surgeon to precisely remove tissue around nerves or bone.

In addition to the above, applicant has discovered that the Coblation™ mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break. Accordingly, the present invention in its current configuration generally does not ablate or remove such fatty tissue. Of course, factors may be changed such that these double bonds can be broken (e.g., increasing voltage or changing the electrode configuration to increase the current density at the electrode tips).

In another aspect of the invention, a loop electrode is employed to resect, shape or otherwise remove tissue fragments from the treatment site, and one or more electrode terminals are employed to ablate (i.e., break down the tissue by processes including molecular dissociation or disintegration) the non-ablated tissue fragments in situ. Once a tissue fragment is cut, partially ablated or resected by the loop electrode, one or more electrode terminals will be brought into close proximity to these fragments (either by moving the probe into position, or by drawing the fragments to the electrode terminals with a suction lumen). Voltage is applied between the electrode terminals and the return electrode to volumetrically remove the fragments through molecular dissociation, as described above. The loop electrode and the electrode terminals are preferably electrically isolated such that, for example, current can be limited (passively or actively) or completely interrupted to the loop electrode as the surgeon employs the electrode terminals to ablate tissue fragments (and vice versa).

In another aspect of the invention, the loop electrode(s) are employed only to ablate tissue using the Coblation™ mechanisms described above. In these embodiments, the loop electrode(s) provides a relatively uniform smooth cutting or ablation effect across the tissue. In addition, loop electrodes generally have a larger surface area exposed to electrically conductive fluid (as compared to the smaller electrode terminals described above), which increases the rate of ablation of tissue. Preferably, the loop electrode(s) extend a sufficient distance from the electrode support member selected to achieve a desirable ablation rate, while minimizing power dissipation into the surrounding medium (which could cause undesirable thermal damage to surrounding or underlying tissue). In an exemplary embodiment, the loop electrode has a length from one end to the other end of about 0.5 to 20 mm, usually about 1 to 8 mm. The loop electrode usually extends about 0.25 to 10 mm from the distal end of the support member, preferably about 1 to 4 mm.

The loop electrode(s) may have a variety of cross-sectional shapes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be removed along the length of a solid or hollow wire electrode to form D or C shaped wires, respectively, with edges facing in the cutting direction. Alternatively, material can be removed at closely spaced intervals along the electrode length to form transverse grooves, slots, threads or the like along the electrodes.

In some embodiments, the loop electrode(s) will have a "non-active" portion or surface to selectively reduce undesirable current flow from the non-active portion or surface into tissue or surrounding electrically conducting liquids (e.g., isotonic saline, blood or blood/non-conducting irrigant mixtures). Preferably, the "non-active" electrode portion will be coated with an electrically insulating material. This can be accomplished, for example, with plasma deposited coatings of an insulating material, thin-film deposition of an insulating material using evaporative or sputtering techniques (e.g., SiO2 or Si3N4), dip coating, or by providing an electrically insulating support member to electrically insulate a portion of the external surface of the electrode. The electrically insulated nonactive portion of the active electrode(s) allows the surgeon to selectively resect and/or ablate tissue, while minimizing necrosis or ablation of surrounding non-target tissue or other body structures.

In addition, the loop electrode(s) may comprise a single electrode extending from first and second ends to an insulating support in the shaft, or multiple, electrically isolated electrodes extending around the loop. One or more return electrodes may also be positioned along the loop portion. Further descriptions of these configurations can be found in U.S. application Ser. No. 08/687792, filed on Jul. 18, 1996, which as already been incorporated herein by reference.

The electrosurgical probe will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. The distal portion of the shaft may comprise a flexible material, such as plastics, malleable stainless steel, etc, so that the physician can mold the distal portion into different configurations for different applications. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Thus, the shaft will typically have a length of at least 5 cm for oral procedures and at least 10 cm, more typically being 20 cm, or longer for endoscopic procedures. The shaft will typically have a diameter of at least 0.5 mm and frequently in the range from 1 to 10 mm. Of course, for dermatological procedures on the outer skin, the shaft may have any suitable length and diameter that would facilitate handling by the surgeon.

For procedures within the nose, the shaft will have a suitable diameter and length to allow the surgeon to reach the target site (e.g., a blockage in the nasal cavity or one of the sinuses) by delivering the probe shaft through one of the nasal passages or another opening (e.g., an opening in the eye or through an opening surgically creating during the procedure). Thus, the shaft will usually have a length in the range of about 5–25 cm, and a diameter in the range of about 0.5 to 5 mm. For procedures requiring the formation of a small hole or channel in tissue, such as treating swollen turbinates, the shaft diameter will usually be less than 3 mm, preferably less than about 1 mm. Likewise, for procedures in the ear, the shaft should have a length in the range of about 3 to 20 cm, and a diameter of about 0.3 to 5 mm. For procedures in the mouth or upper throat, the shaft will have any suitable length and diameter that would facilitate handling by the surgeon. For procedures in the lower throat, such as laryngectomies, the shaft will be suitably designed to access the larynx. For example, the shaft may be flexible, or have a distal bend to accommodate the bend in the patient's throat. In this regard, the shaft may be a rigid shaft having a specifically designed bend to correspond with the geometry of the mouth and throat, or it may have a flexible distal end, or it may be part of a catheter. In any of these embodiments, the shaft may also be introduced through rigid or flexible endoscopes. Specific shaft designs will be described in detail in connection with the figures hereinafter.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode. A more complete description of an exemplary method of directing electrically conducting fluid between the active and return electrodes is described in parent application Ser. No. 08/485,219, filed Jun. 7, 1995, previously incorporated herein by reference.

In some procedures, it may also be necessary to retrieve or aspirate the electrically conductive fluid after it has been directed to the target site. For example, in procedures in the nose, mouth or throat, it may be desirable to aspirate the fluid so that it does not flow down the patient's throat. In addition, it may be desirable to aspirate small pieces of tissue that are not completely disintegrated by the high frequency energy, or other fluids at the target site, such as blood, mucus, the gaseous products of ablation, etc. Accordingly, the system of the present invention will usually include a suction lumen in the probe, or on another instrument, for aspirating fluids from the target site.

In some embodiments, the probe will include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation electrode terminal(s), or the same electrode(s) may serve both functions. In some embodiments, the probe will be designed to use suction force to draw loose tissue, such as synovial tissue to the aspiration or ablation electrode(s) on the probe, which are then energized to ablate the loose tissue.

The present invention may use a single active electrode terminal or an electrode array distributed over a contact surface of a probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least two isolated electrode terminals, preferably at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. Active electrode surfaces can have areas in the range from 0.25 $mm^2$ to 75 $mm^2$, usually being from about 0.5 $mm^2$ to 40 $mm^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

In the representative embodiments, the electrode terminals comprise substantially rigid wires protruding outward from the tissue treatment surface of the electrode support member. Usually, the wires will extend about 0.1 to 4.0 mm, preferably about 0.2 to 1 mm, from the distal surface of the support member. In the exemplary embodiments, the electrosurgical probe includes between about two to fifty electrically isolated electrode terminals, and preferably between about three to twenty electrode terminals.

The electrically conducting fluid should have a threshold conductivity to provide a suitable conductive path between the return electrode(s) and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The voltage applied between the return electrode(s) and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular FESS procedure, arthroscopic surgery, dermatological procedure, ophthalmic procedures, open surgery or other endoscopic surgery procedure. A description of a suitable power source can be found in Provisional Application No. 60/062,97, filed on Oct. 23, 1997, the complete disclosure of which has been incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,0000 uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source. The active electrode may have a ball shape (e.g., for tissue vaporization and desiccation), a twizzle shape (for vaporization and needle-like cutting), a spring shape (for rapid tissue debulking and desiccation), a twisted metal shape, an annular or solid tube shape or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode or the like. In one embodiment, the probe comprises a single active electrode terminal that extends from an insulating member, e.g., ceramic, at the distal end of the probe. The insulating member is preferably a tubular structure that separates the active electrode terminal from a tubular or annular return electrode positioned proximal to the insulating member and the active electrode.

Referring now to FIG. 1, an exemplary electrosurgical system 5 for resection, ablation, coagulation and/or contraction of tissue will now be described in detail. As shown, electrosurgical system 5 generally includes an electrosurgical probe 20 connected to a power supply 10 for providing high frequency voltage to one or more electrode terminals and a loop electrode (not shown in FIG. 1) on probe 20. Probe 20 includes a connector housing 44 at its proximal end, which can be removably connected to a probe receptacle 32 of a probe cable 22. The proximal portion of cable 22 has a connector 34 to couple probe 20 to power supply 10. Power supply 10 has an operator controllable voltage level adjustment 38 to change the applied voltage level, which is observable at a voltage level display 40. Power supply 10 also includes one or more foot pedals 24 and a cable 26 which is removably coupled to a receptacle 30 with a cable connector 28. The foot pedal 24 may also include a second pedal (not shown) for remotely adjusting the energy level applied to electrode terminals 104, and a third pedal (also not shown) for switching between an ablation mode and a coagulation mode. The specific design of a power supply which may be used with the electrosurgical probe of the present invention is described in Provisional patent application. 60/062,997, Filed Oct. 23, 1997, the full disclosure of which has previously been incorporated herein by reference.

Figure 2:
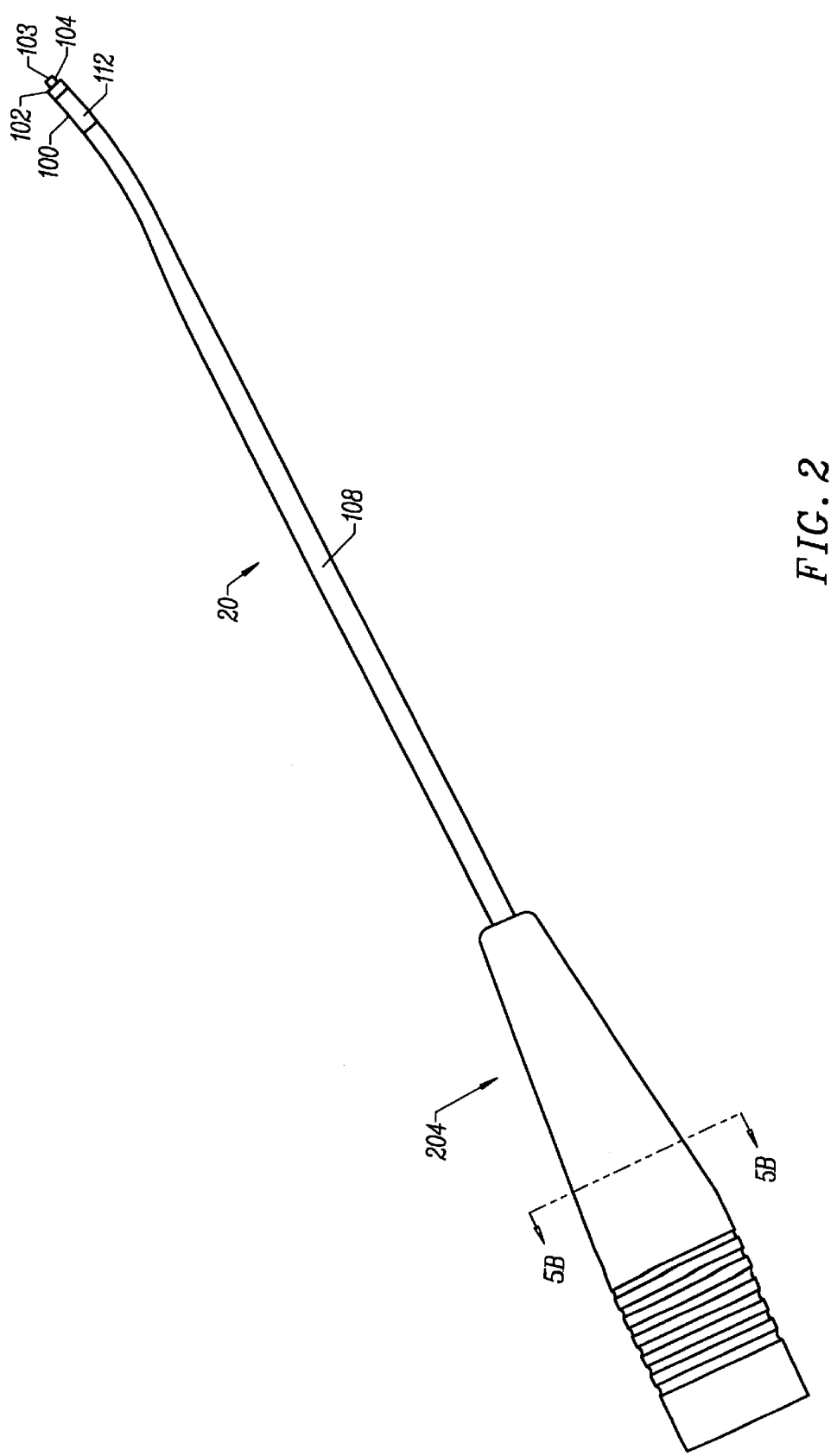
FIG. 2 is a side view of an electrosurgical probe according to the present invention incorporating a loop electrode for resection and ablation of tissue.

FIGS. 2–5 illustrate an exemplary electrosurgical probe 20 constructed according to the principles of the present invention. As shown in FIG. 2, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises an electrically conducting material, usually metal, which is selected from the group consisting of tungsten, stainless steel alloys, platinum or its alloys, titanium or its alloys, molybdenum or its alloys, and nickel or its alloys. Shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Figure 3:
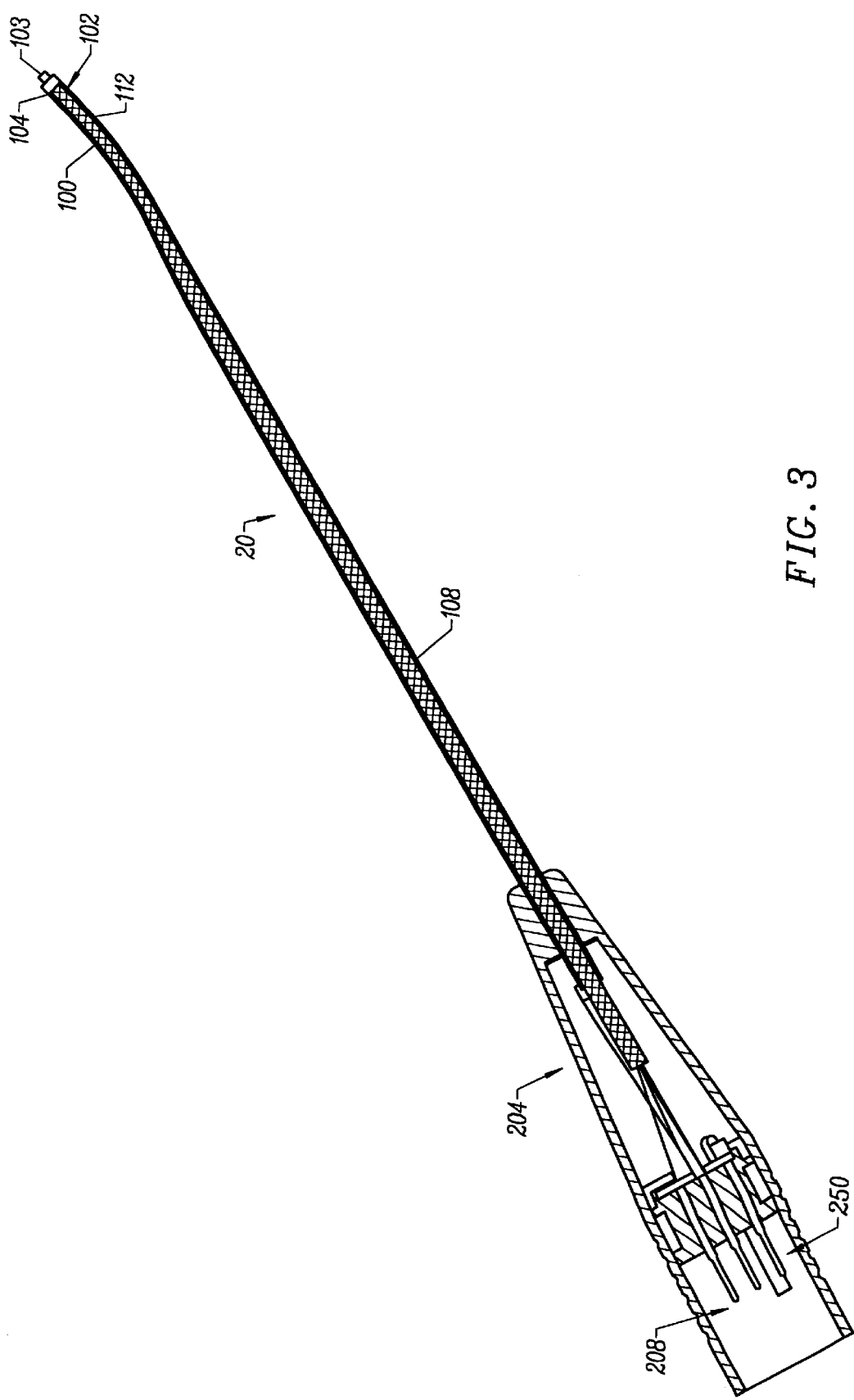
FIG. 3 is a cross sectional view of the electrosurgical probe of FIG. 1.

Handle 204 typically comprises a plastic material that is easily molded into a suitable shape for handling by the surgeon. As shown in FIG. 3, handle 204 defines an inner cavity 208 that houses the electrical connections 250 (discussed below), and provides a suitable interface for connection to an electrical connecting cable 22 (see FIG. 1). As shown in FIG. 5B, the probe will also include a coding resistor 400 having a value selected to program different output ranges and modes of operation for the power supply. This allows a single power supply to be used with a variety of different probes in different applications (e.g., dermatology, cardiac surgery, neurosurgery, arthroscopy, etc). Electrode support member 102 extends from the distal end of shaft 100 (usually about 1 to 20 mm), and provides support for a loop electrode 103 and a plurality of electrically isolated electrode terminals 104 (see FIG. 4).

As shown in FIG. 3, the distal portion of shaft 100 is preferably bent to improve access to the operative site of the tissue being treated (e.g., contracted). Electrode support member 102 has a substantially planar tissue treatment surface 212 (see FIG. 4) that is usually at an angle of about 10 to 90 degrees relative to the longitudinal axis of shaft 100, preferably about 10 to 30 degrees and more preferably about 15–18 degrees. In addition, the distal end of the shaft may have a bevel, as described in commonly-assigned patent application Ser. No. 562,332 filed Nov. 22, 1995. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in PCT International Application, U.S. National Phase Ser. No. PCT/US94/05168.

The bend in the distal portion of shaft 100 is particularly advantageous in arthroscopic treatment of joint tissue as it allows the surgeon to reach the target tissue within the joint as the shaft 100 extends through a cannula or portal. Of course, it will be recognized that the shaft may have different angles depending on the procedure. For example, a shaft having a 90° bend angle may be particularly useful for accessing tissue located in the back portion of a joint compartment and a shaft having a 10° to 30° bend angle may be useful for accessing tissue near or in the front portion of the joint compartment.

Figure 4:
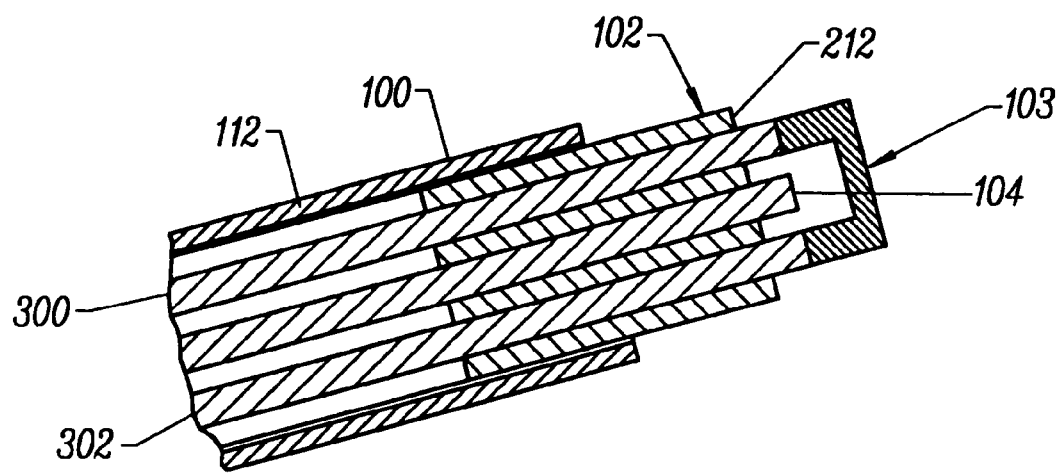
FIG. 4 is an exploded view of a proximal portion of the electrosurgical probe.
Figure 5B:
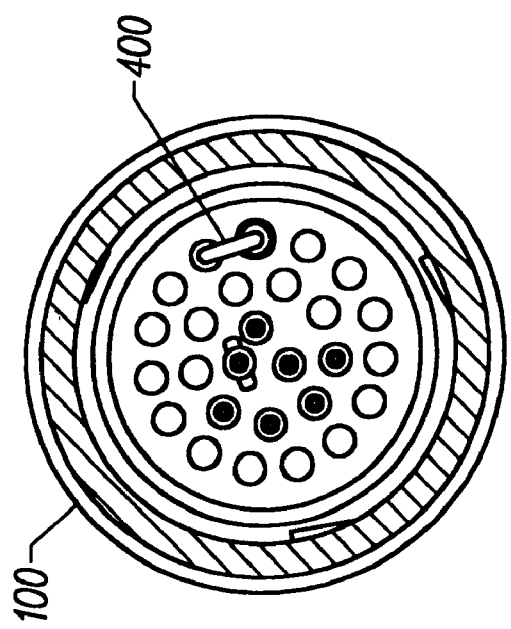
FIGS. 5A and 5B are end and cross-sectional views, respectively, of the proximal portion of the probe.
Figure 5A:
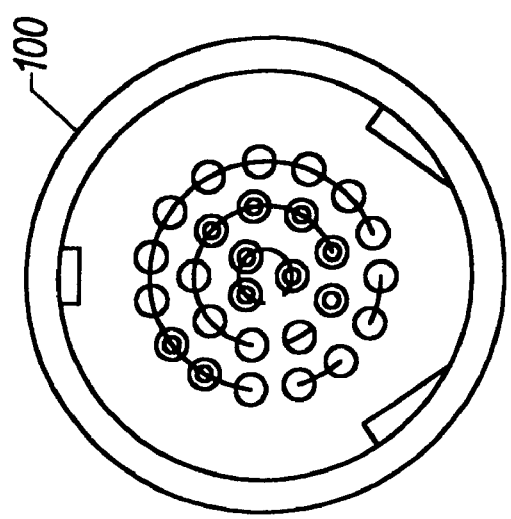

As shown in FIG. 4, loop electrode 103 has first and second ends extending from the electrode support member 103. The first and second ends are coupled to, or integral with, a pair of connectors 300, 302, e.g., wires, that extend through the shaft of the probe to its proximal end for coupling to the high frequency power supply. The loop electrode usually extends about 0.5 to about 10 mm from the distal end of support member, preferably about 1 to 2 mm. In the representative embodiment, the loop electrode has a solid construction with a substantially uniform cross-sectional area, e.g., circular, square, etc. Of course, it will be recognized that the ablation electrode may have a wide variety of cross-sectional shapes, such as annular, square, rectangular, L-shaped, V-shaped, D-shaped, C-shaped, star-shaped and crossed-shaped, as described in commonly-assigned co-pending application Ser. No. 08/687792. In addition, it should be noted that loop electrode 103 may have a geometry other than that shown in FIGS. 2–5, such as a semi-circular loop, a V-shaped loop, a straight wire electrode extending between two support members, and the like. Also, loop electrode may be positioned on a lateral surface of the shaft, or it may extend at a transverse angle from the distal end of the shaft, depending on the particular surgical procedure.

Loop electrode 103 usually extends further away from the support member than the electrode terminals 104 to facilitate resection and ablation of tissue. As discussed below, loop electrode 103 is especially configured for resecting fragments or pieces of tissue, while the electrode terminals ablate or cause molecular dissociation or disintegration of the removed pieces from the fluid environment. In the presently preferred embodiment, the probe will include 3 to 7 electrode terminals positioned on either side of the loop electrode. The probe may further include a suction lumen (not shown) for drawing the pieces of tissue toward the electrode terminals after they have been removed from the target site by the loop electrode 103.

Referring to FIG. 4, the electrically isolated electrode terminals 104 are preferably spaced apart over tissue treatment surface 212 of electrode support member 102. The tissue treatment surface and individual electrode terminals 104 will usually have dimensions within the ranges set forth above. In the representative embodiment, the tissue treatment surface 212 has an oval cross-sectional shape with a length L in the range of 1 mm to 20 mm and a width W in the range from 0.3 mm to 7 mm. The oval cross-sectional shape accommodates the bend in the distal portion of shaft 202. The electrode terminals 104 preferably extend slightly outward from surface 212, typically by a distance from 0.2 mm to 2. However, it will be understood that terminals 104 may be flush with this surface, or even recessed, if desired. In one embodiment of the invention, the electrode terminals are axially adjustable relative to the tissue treatment surface so that the surgeon can adjust the distance between the surface and the electrode terminals.

In the embodiment shown in FIGS. 2–5, probe 20 includes a return electrode 112 for completing the current path between electrode terminals 104, loop electrode 103 and a high frequency power supply 10 (see FIG. 1). As shown, return electrode 112 preferably comprises an annular exposed region of shaft 102 slightly proximal to tissue treatment surface 212 of electrode support member 102, typically about 0.5 to 10 mm and more preferably about 1 to 10 mm. Return electrode 112 is coupled to a connector 258 that extends to the proximal end of probe 10, where it is suitably connected to power supply 10 (FIG. 1).

As shown in FIG. 2, return electrode 112 is not directly connected to electrode terminals 104 and loop electrode 103. To complete this current path, electrically conducting fluid (e.g., isotonic saline) is caused to flow therebetween. In the representative embodiment, the electrically conducting fluid is delivered from a fluid delivery element (not shown) that is separate from probe 20. In arthroscopic surgery, for example, the body cavity will be flooded with isotonic saline and the probe 20 will be introduced into this flooded cavity. Electrically conducting fluid will be continually resupplied to maintain the conduction path between return electrode 112 and electrode terminals 104 and loop electrode 103.

In alternative embodiments, the fluid path may be formed in probe 20 by, for example, an inner lumen or an annular gap (not shown) between the return electrode and a tubular support member within shaft 100. This annular gap may be formed near the perimeter of the shaft 100 such that the electrically conducting fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 20 via a fluid supply tube (not shown) that may or may not have a controllable valve. A more complete description of an electrosurgical probe incorporating one or more fluid lumen(s) can be found in commonly assigned, co-pending application Ser. No. 08/485, 219, filed on Jun. 7, 1995, the complete disclosure of which has previously been incorporated herein by reference.

In addition, the probe 20 may include an aspiration lumen (not shown) for aspirating excess conductive fluid, other fluids, such as blood, and/or tissue fragments from the target site. The probe may also include one or more aspiration electrode(s), such as those described below in reference to FIGS. 8–12, for ablating the aspirated tissue fragments. Alternatively, the aspiration electrode(s) may comprise the active electrode terminals described above. For example, the probe may have an aspiration lumen with a distal opening positioned adjacent one or more of the active electrode terminals at the distal end of the probe. As tissue fragments are drawn into the aspiration lumen, the active electrode terminals are energized to ablate at least a portion of these fragments to inhibit clogging of the lumen.

Figure 6:
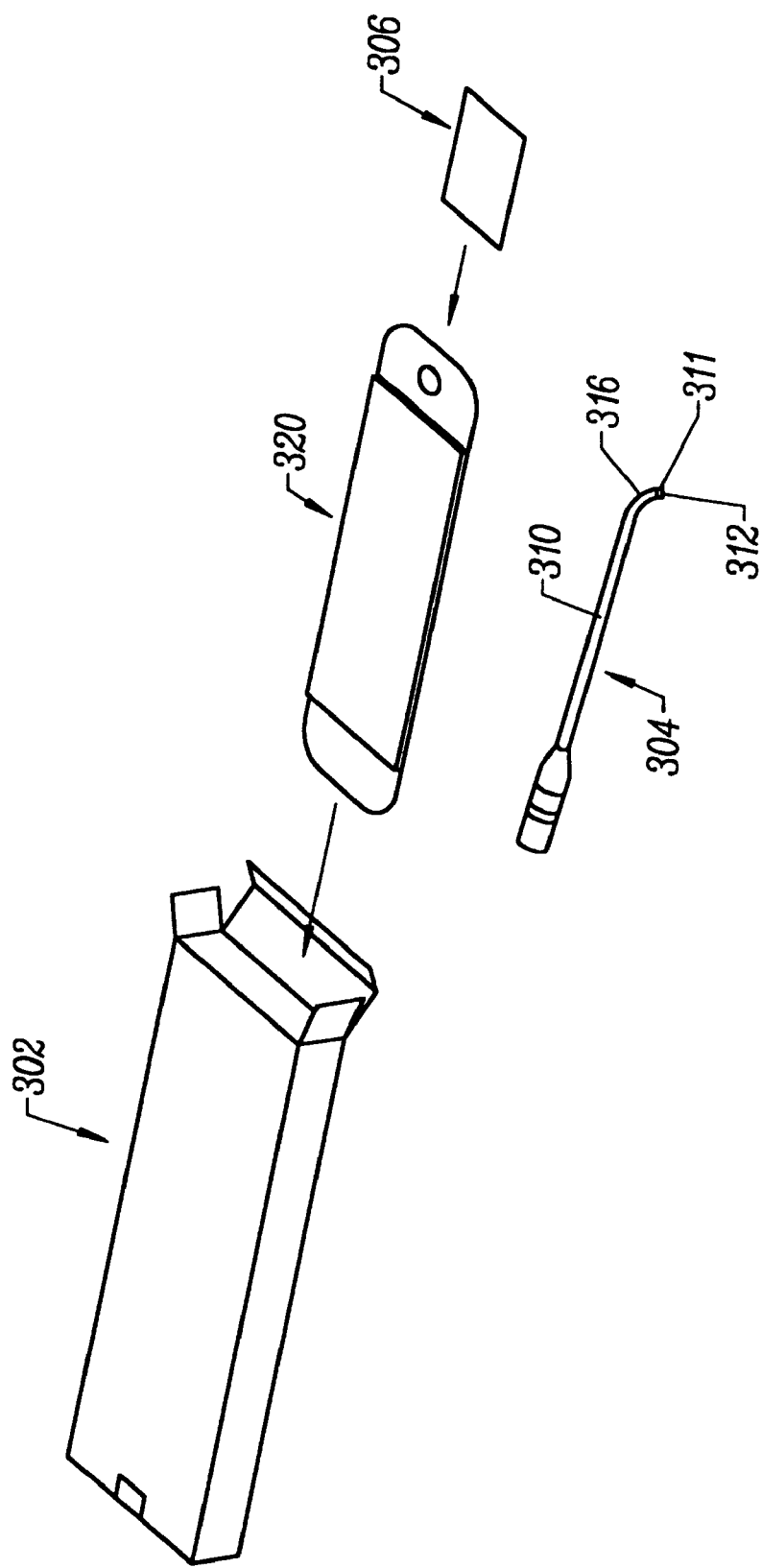
FIG. 6 illustrates a surgical kit for removing and ablating tissue according to the present invention.

Referring now to FIG. 6, a surgical kit 300 for resecting and/or ablating tissue within a joint according to the invention will now be described. As shown, surgical kit 300 includes a package 302 for housing a surgical instrument 304, and an instructions for use 306 of instrument 304. Package 302 may comprise any suitable package, such as a box, carton, wrapping, etc. In the exemplary embodiment, kit 300 further includes a sterile wrapping 320 for packaging and storing instrument 304. Instrument 304 includes a shaft 310 having at least one loop electrode 311 and at least one electrode terminal 312 at its distal end, and at least one connector (not shown) extending from loop electrode 311 and electrode terminal 312 to the proximal end of shaft 310. The instrument 304 is generally disposable after a single procedure. Instrument 304 may or may not include a return electrode 316.

The instructions for use 306 generally includes the steps of adjusting a voltage level of a high frequency power supply (not shown) to effect resection and/or ablation of tissue at the target site, connecting the surgical instrument 304 to the high frequency power supply, positioning the loop electrode 311 and the electrode terminal 312 within electrically conductive fluid at or near the tissue at the target site, and activating the power supply. The voltage level is usually about 40 to 400 volts rms for operating frequencies of about 100 to 200 kHz. In the preferred embodiment, the positioning step includes introducing at least a distal portion of the instrument 304 through a portal into a joint.

The present invention is particularly useful for lateral release procedures, or for resecting and ablating a buckethandle tear of the medial meniscus. In the latter technique, the probe is introduced through a medial port and the volume which surrounds the working end of the probe is filled with an electrically conductive fluid which may, by way of example, be isotonic saline or other biocompatible, electrically conductive irrigant solution. When a voltage is applied between the loop electrode and the return electrode, electrical current flows from the loop electrode, through the irrigant solution to the return electrode. The anterior horn is excised by pressing the exposed portion of the loop electrode into the tear and removing one or more tissue fragments. The displaced fragments are then ablated with the electrode terminals as described above.

Through a central patellar splitting approach, the probe is then placed within the joint through the intercondylar notch, and the attached posterior horn insertion is resected by pressing the loop electrode into the attached posterior fragment. The fragment is then removed with the electrode terminals and the remnant is checked for stability.

Figure 7:
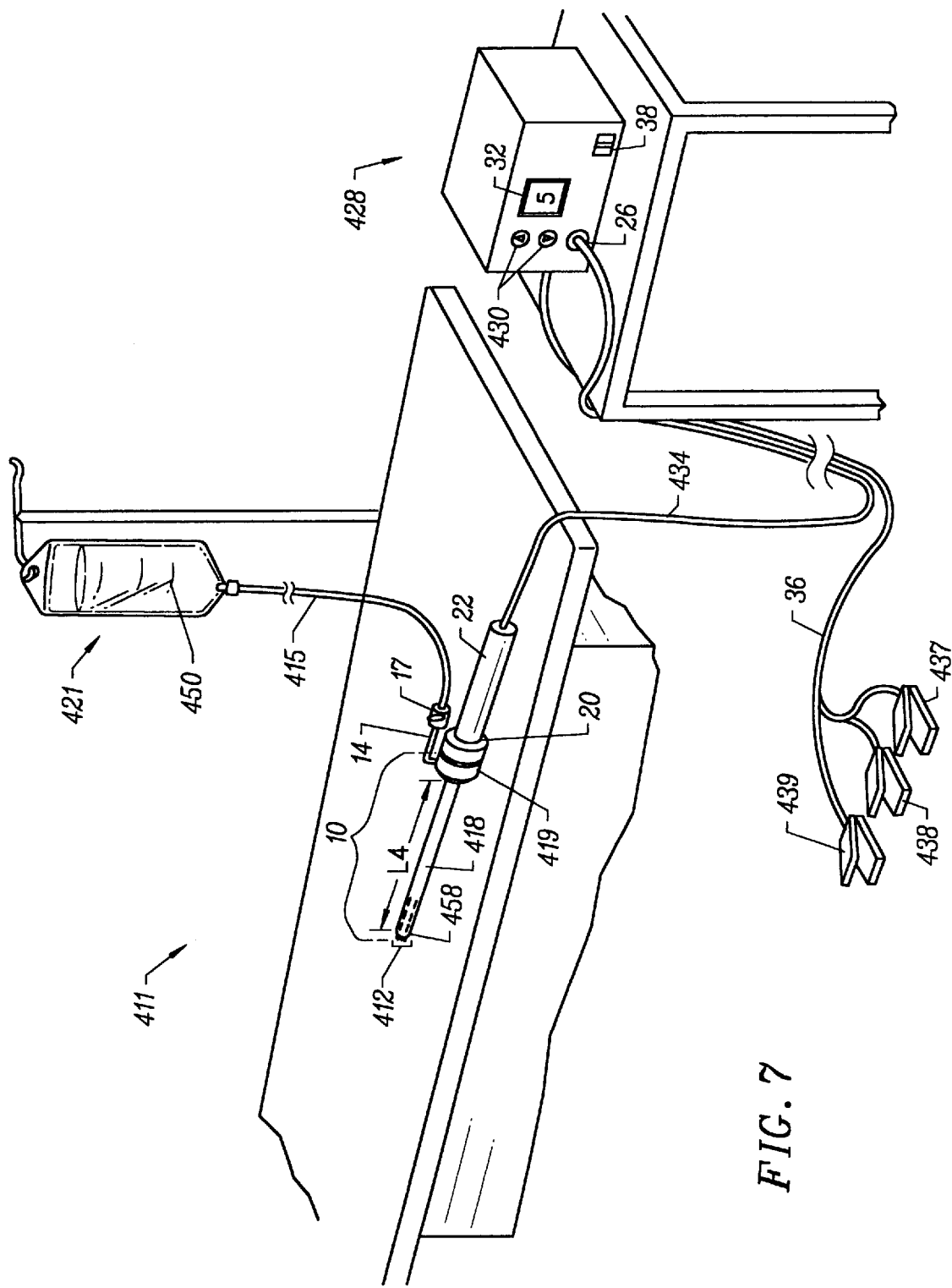
FIG. 7 is a perspective view of another electrosurgical system incorporating a power supply, an electrosurgical probe and a supply of electrically conductive fluid for delivering the fluid to the target site.

Referring now to FIG. 7, an exemplary electrosurgical system 411 for treatment of tissue in 'dry fields' will now be described in detail. Of course, system 411 may also be used in 'wet field', i.e., the target site is immersed in electrically conductive fluid. However, this system is particularly useful in 'dry fields' where the fluid is preferably delivered through electrosurgical probe to the target site. As shown, electrosurgical system 411 generally comprises an electrosurgical handpiece or probe 410 connected to a power supply 428 for providing high frequency voltage to a target site and a fluid source 421 for supplying electrically conducting fluid 450 to probe 410. In addition, electrosurgical system 411 may include an endoscope (not shown) with a fiber optic head light for viewing the surgical site, particularly in sinus procedures or procedures in the ear or the back of the mouth. The endoscope may be integral with probe 410, or it may be part of a separate instrument. The system 411 may also include a vacuum source (not shown) for coupling to a suction lumen or tube 505 (see FIG. 2) in the probe 410 for aspirating the target site.

As shown, probe 410 generally includes a proximal handle 419 and an elongate shaft 418 having an array 412 of electrode terminals 458 at its distal end. A connecting cable 434 has a connector 426 for electrically coupling the electrode terminals 458 to power supply 428. The electrode terminals 458 are electrically isolated from each other and each of the terminals 458 is connected to an active or passive control network within power supply 428 by means of a plurality of individually insulated conductors (not shown). A fluid supply tube 415 is connected to a fluid tube 414 of probe 410 for supplying electrically conducting fluid 450 to the target site.

Similar to the above embodiment, power supply 428 has an operator controllable voltage level adjustment 430 to change the applied voltage level, which is observable at a voltage level display 432. Power supply 428 also includes first, second and third foot pedals 437, 438, 439 and a cable 436 which is removably coupled to power supply 428. The foot pedals 37, 38, 39 allow the surgeon to remotely adjust the energy level applied to electrode terminals 458. In an exemplary embodiment, first foot pedal 437 is used to place the power supply into the "ablation" mode and second foot pedal 438 places power supply 428 into the "coagulation" mode. The third foot pedal 439 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 430 or third foot pedal 439 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 428 applies a low enough voltage to the electrode terminals (or the coagulation electrode) to avoid vaporization of the electrically conductive fluid and subsequent molecular dissociation of the tissue. The surgeon may automatically toggle the power supply between the ablation and coagulation modes by alternatively stepping on foot pedals 437, 438, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 437. A specific design of a suitable power supply for use with the present invention can be found in provisional patent application No. 06/062,997, Filed Oct. 23, 1997, filed Oct. 23, 1997, previously incorporated herein by reference.

Figure 8:
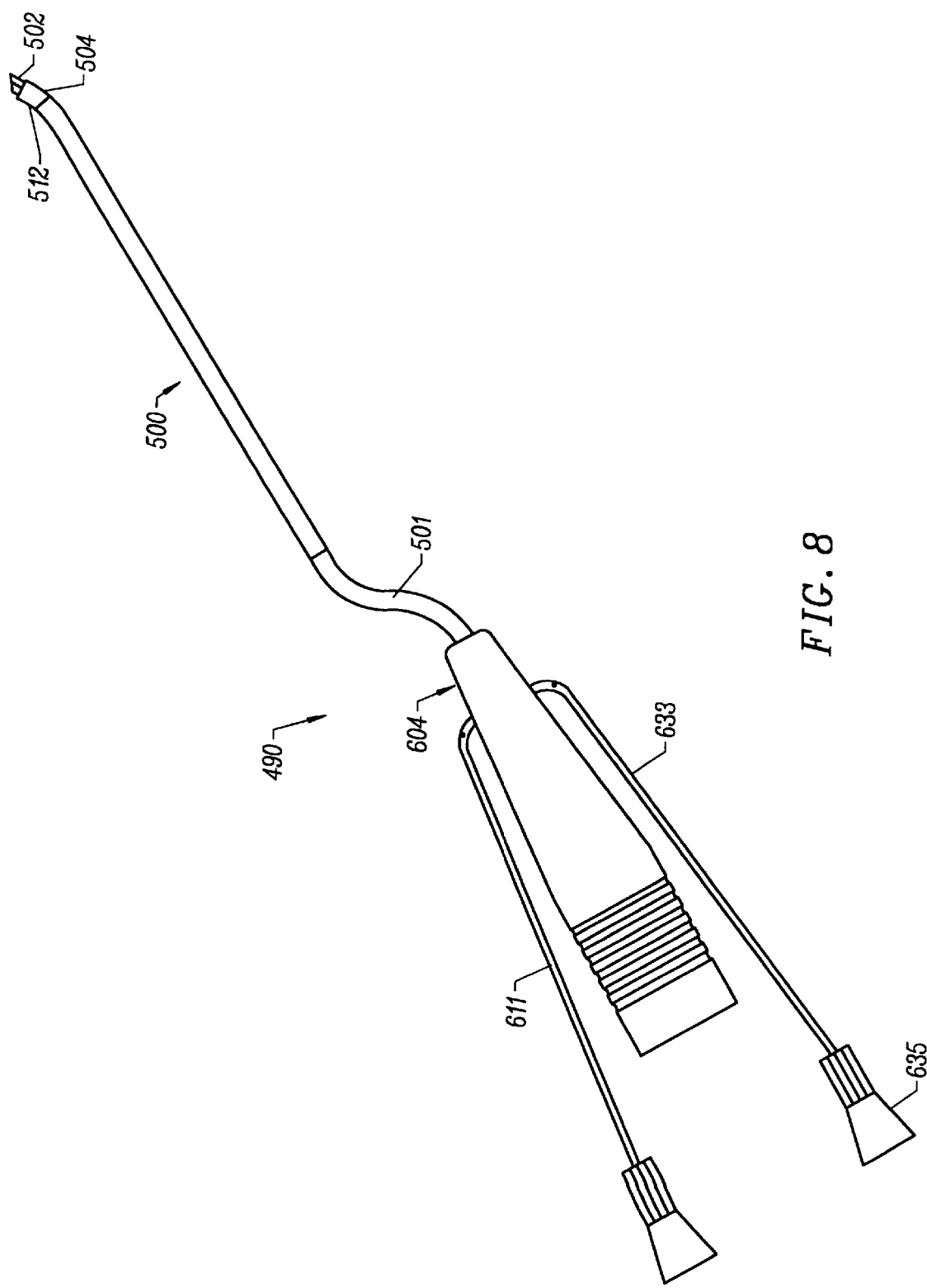
FIG. 8 is a side view of another electrosurgical probe according to the present invention incorporating aspiration electrodes for ablating aspirated tissue fragments and/or tissue strands, such as synovial tissue.
Figure 9:
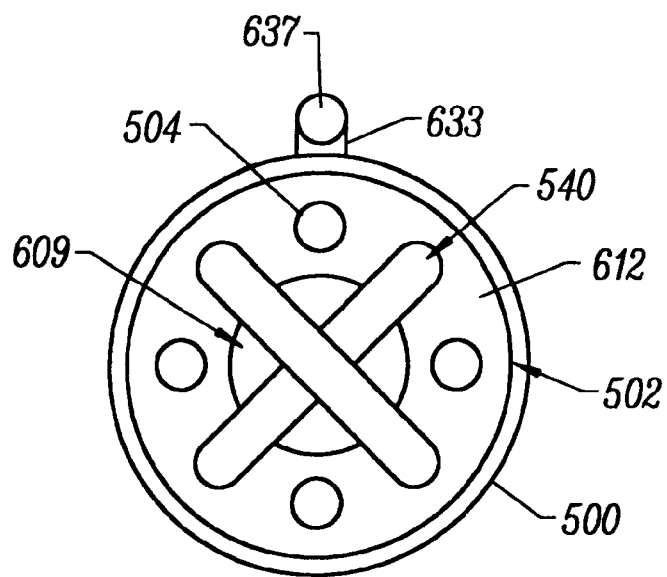
FIG. 9 is an end view of the probe of FIG. 8.
Figure 10:
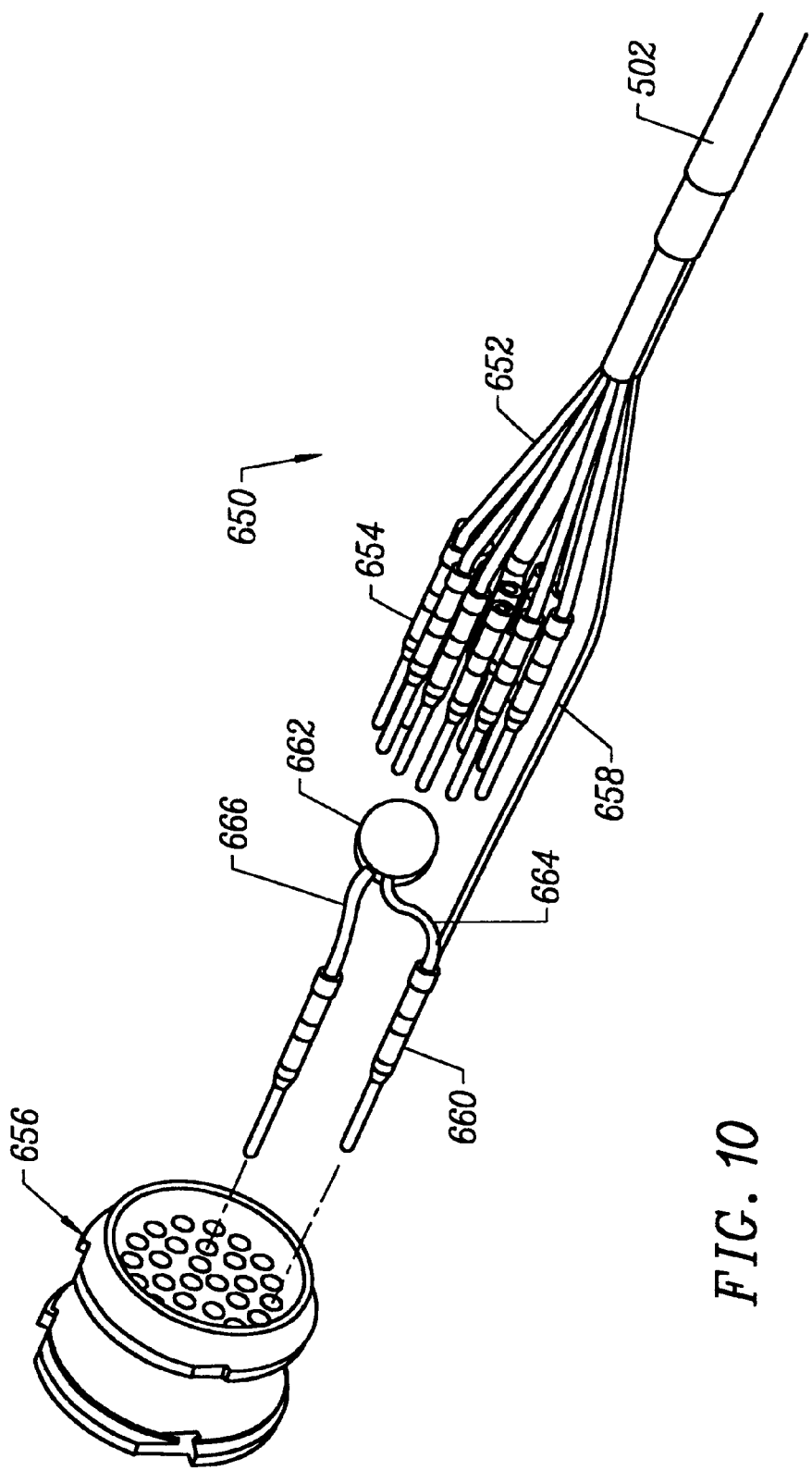
FIG. 10 is an exploded view of a proximal portion of the electrosurgical probe.

FIGS. 8–10 illustrate an exemplary electrosurgical probe 490 constructed according to the principles of the present invention. As shown in FIG. 2, probe 490 generally includes an elongated shaft 500 which may be flexible or rigid, a handle 604 coupled to the proximal end of shaft 500 and an electrode support member 502 coupled to the distal end of shaft 500. Shaft 500 preferably includes a bend 501 that allows the distal section of shaft 500 to be offset from the proximal section and handle 604. This offset facilitates procedures that require an endoscope, such as FESS, because the endoscope can, for example, be introduced through the same nasal passage as the shaft 500 without interference between handle 604 and the eyepiece of the endoscope (see FIG. 16). Shaft 500 preferably comprises a plastic material that is easily molded into the shape shown in FIG. 1.

In an alternative embodiment (not shown), shaft 500 comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 500 includes an electrically insulating jacket 508, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Handle 604 typically comprises a plastic material that is easily molded into a suitable shape for handling by the surgeon. Handle 604 defines an inner cavity (not shown) that houses the electrical connections 650 (FIG. 10), and provides a suitable interface for connection to an electrical connecting cable 22 (see FIG. 7). Electrode support member 502 extends from the distal end of shaft 500 (usually about 1 to 20 mm), and provides support for a plurality of electrically isolated electrode terminals 504 (see FIG. 9). As shown in FIG. 8, a fluid tube 633 extends through an opening in handle 604, and includes a connector 635 for connection to a fluid supply source, for supplying electrically conductive fluid to the target site. Depending on the configuration of the distal surface of shaft 500, fluid tube 633 may extend through a single lumen (not shown) in shaft 500, or it may be coupled to a plurality of lumens (also not shown) that extend through shaft 500 to a plurality of openings at its distal end. In the representative embodiment, fluid tube 633 extends along the exterior of shaft 500 to a point just proximal of return electrode 512 (see FIG. 9). In this embodiment, the fluid is directed through an opening 637 past return electrode 512 to the electrode terminals 504. Probe 490 may also include a valve 417 (FIG. 1) or equivalent structure for controlling the flow rate of the electrically conducting fluid to the target site.

As shown in FIG. 8, the distal portion of shaft 500 is preferably bent to improve access to the operative site of the tissue being treated. Electrode support member 502 has a substantially planar tissue treatment surface 612 that is usually at an angle of about 10 to 90 degrees relative to the longitudinal axis of shaft 600, preferably about 30 to 60 degrees and more preferably about 45 degrees. In alternative embodiments, the distal portion of shaft 500 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in PCT International Application, U.S. National Phase Serial No. PCT/US94/05168, filed on May 10, 1994, now U.S. Pat. No. 5,697,909, the complete disclosure of which has previously been incorporated herein by reference.

The bend in the distal portion of shaft 500 is particularly advantageous in the treatment of sinus tissue as it allows the surgeon to reach the target tissue within the nose as the shaft 500 extends through the nasal passage. Of course, it will be recognized that the shaft may have different angles depending on the procedure. For example, a shaft having a 90° bend angle may be particularly useful for accessing tissue located in the back portion of the mouth and a shaft having a 10° to 30° bend angle may be useful for accessing tissue near or in the front portion of the mouth or nose In the embodiment shown in FIGS. 8–10, probe 490 includes a return electrode 512 for completing the current path between electrode terminals 504 and a high frequency power supply 28 (see FIG. 1). As shown, return electrode 512 preferably comprises an annular conductive band coupled to the distal end of shaft 500 slightly proximal to tissue treatment surface 612 of electrode support member 502, typically about 0.5 to 10 mm and more preferably about 1 to 10 mm. Return electrode 512 is coupled to a connector 658 that extends to the proximal end of probe 410, where it is suitably connected to power supply 410 (FIG. 7).

As shown in FIG. 8, return electrode 512 is not directly connected to electrode terminals 504. To complete this current path so that electrode terminals 504 are electrically connected to return electrode 512, electrically conducting fluid (e.g., isotonic saline) is caused to flow therebetween. In the representative embodiment, the electrically conducting fluid is delivered through fluid tube 633 to opening 637, as described above.

Alternatively, the fluid may be delivered by a fluid delivery element (not shown) that is separate from probe 490. In arthroscopic surgery, for example, the body cavity will be flooded with isotonic saline and the probe 490 will be introduced into this flooded cavity. Electrically conducting fluid will be continually resupplied to maintain the conduction path between return electrode 512 and electrode terminals 504.

In alternative embodiments, the fluid path may be formed in probe 490 by, for example, an inner lumen or an annular gap between the return electrode and a tubular support member within shaft 500. This annular gap may be formed near the perimeter of the shaft 500 such that the electrically conducting fluid tends to flow radially inward towards the target site, or it may be formed towards the center of shaft 500 so that the fluid flows radially outward. In both of these embodiments, a fluid source (e.g., a bag of fluid elevated above the surgical site or having a pumping device), is coupled to probe 490 via a fluid supply tube (not shown) that may or may not have a controllable valve. A more complete description of an electrosurgical probe incorporating one or more fluid lumen(s) can be found in parent application Ser. No. 08/485,219, filed on Jun. 7, 1995, the complete disclosure of which has previously been incorporated herein by reference.

Referring to FIG. 9, the electrically isolated electrode terminals 504 are spaced apart over tissue treatment surface 612 of electrode support member 502. The tissue treatment surface and individual electrode terminals 504 will usually have dimensions within the ranges set forth above. As shown, the probe includes a single, larger opening 609 in the center of tissue treatment surface 612, and a plurality of electrode terminals (e.g., about 3–15) around the perimeter of surface 612 (see FIG. 9).

Alternatively, the probe may include a single, annular, or partially annular, electrode terminal at the perimeter of the tissue treatment surface. The central opening 609 is coupled to a suction lumen (not shown) within shaft 500 and a suction tube 611 (FIG. 8) for aspirating tissue, fluids and/or gases from the target site. In this embodiment, the electrically conductive fluid generally flows radially inward past electrode terminals 504 and then back through the opening 609. Aspirating the electrically conductive fluid during surgery allows the surgeon to see the target site, and it prevents the fluid from flowing into the patient's body, e.g., through the sinus passages, down the patient's throat or into the ear canal.

As shown, one or more of the electrode terminals 504 comprise loop electrodes 540 that extend across distal opening 609 of the suction lumen within shaft 500. In the representative embodiment, two of the electrode terminals 504 comprise loop electrodes 540 that cross over the distal opening 609. Of course, it will be recognized that a variety of different configurations are possible, such as a single loop electrode, or multiple loop electrodes having different configurations than shown. In addition, the electrodes may have shapes other than loops, such as the coiled configurations shown in FIGS. 11 and 12. Alternatively, the electrodes may be formed within suction lumen proximal to the distal opening 609, as shown in FIG. 13. The main function of loop electrodes 540 is to ablate portions of tissue that are drawn into the suction lumen to prevent clogging of the lumen.

Loop electrodes 540 are electrically isolated from the other electrode terminals 504, which can be referred to hereinafter as the ablation electrodes 504. Loop electrodes 540 may or may not be electrically isolated from each other. Loop electrodes 540 will usually extend only about 0.05 to 4 mm, preferably about 0.1 to 1 mm from the tissue treatment surface of electrode support member 504.

Of course, it will be recognized that the distal tip of probe may have a variety of different configurations. For example, the probe may include a plurality of openings 609 around the outer perimeter of tissue treatment surface 612. In this embodiment, the electrode terminals 504 extend from the center of tissue treatment surface 612 radially inward from openings 609. The openings are suitably coupled to fluid tube 633 for delivering electrically conductive fluid to the target site, and a suction tube 611 for aspirating the fluid after it has completed the conductive path between the return electrode 512 and the electrode terminals 504. In this embodiment, the ablation electrode terminals 504 are close enough to openings 609 to ablate most of the large tissue fragments that are drawn into these openings.

FIG. 10 illustrates the electrical connections 650 within handle 604 for coupling electrode terminals 504 and return electrode 512 to the power supply 428. As shown, a plurality of wires 652 extend through shaft 500 to couple terminals 504 to a plurality of pins 654, which are plugged into a connector block 656 for coupling to a connecting cable 422 (FIG. 1). Similarly, return electrode 512 is coupled to connector block 656 via a wire 658 and a plug 660.

In use, the distal portion of probe 490 is introduced to the target site (either endoscopically, through an open procedure, or directly onto the patient's skin) and electrode terminals 504 are positioned adjacent tissue. Electrically conductive fluid is delivered through tube 633 and opening 637 to the tissue. The fluid flows past the return electrode 512 to the electrode terminals 504 at the distal end of the shaft. The rate of fluid flow is controlled with valve 417 (FIG. 1) such that the zone between the tissue and electrode support 502 is constantly immersed in the fluid. The power supply 428 is then turned on and adjusted such that a high frequency voltage difference is applied between electrode terminals 504 and return electrode 512. The electrically conductive fluid provides the conduction path (see current flux lines) between electrode terminals 504 and the return electrode 512.

In the representative embodiment, the high frequency voltage is sufficient to convert the electrically conductive fluid (not shown) between the target tissue and electrode terminals 504 into an ionized vapor layer or plasma (not shown). As a result of the applied voltage difference between electrode terminal(s) 504 and the target tissue (i.e., the voltage gradient across the plasma layer), charged particles in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e, ablative sublimation) of tissue and the production of low molecular weight gases, such as oxygen, nitrogen, carbon dioxide, hydrogen and methane. The short range of the accelerated charged particles within the tissue confines the molecular dissociation process to the surface layer to minimize damage and necrosis to the underlying tissue.

During the process, the gases will be aspirated through opening 609 and suction tube 611 to a vacuum source. In addition, excess electrically conductive fluid, and other fluids (e.g., blood) will be aspirated from the target site to facilitate the surgeon's view. Applicant has also found that tissue fragments are also aspirated through opening 609 into suction lumen and tube 611 during the procedure. These tissue fragments are ablated or dissociated with loop electrodes 540 with a similar mechanism described above. Namely, as electrically conductive fluid and tissue fragments are aspirated into loop electrodes 540, these electrodes are activated so that high frequency voltage is applied to loop electrodes 540 and return electrode 512 (of course, the probe may include a different, separate return electrode for this purpose). The voltage is sufficient to vaporize the fluid, and create a plasma layer between loop electrodes 540 and the tissue fragments so that portions of the tissue fragments are ablated or removed. This reduces the volume of the tissue fragments as they pass through suction lumen to minimize clogging of the lumen.

In addition, the present invention is particularly useful for removing elastic tissue, such as the synovial tissue found in joints. In arthroscopic procedures, this elastic synovial tissue tends to move away from instruments within the conductive fluid, making it difficult for conventional instruments to remove this tissue. With the present invention, the probe is moved adjacent the target synovial tissue, and the vacuum source is activated to draw the synovial tissue towards the distal end of the probe. The aspiration and/or active electrode terminals are then energized to ablate this tissue. This allows the surgeon to quickly and precisely ablate elastic tissue with minimal thermal damage to the treatment site.

In one embodiment, loop electrodes 540 are electrically isolated from the other electrode terminals 504, and they must be separately activated at the power supply 428. In other embodiments, loop electrodes 540 will be activated at the same time that electrode terminals 504 are activated. In this case, applicant has found that the plasma layer typically forms when tissue is drawn adjacent to loop electrodes 540.

Figure 11:
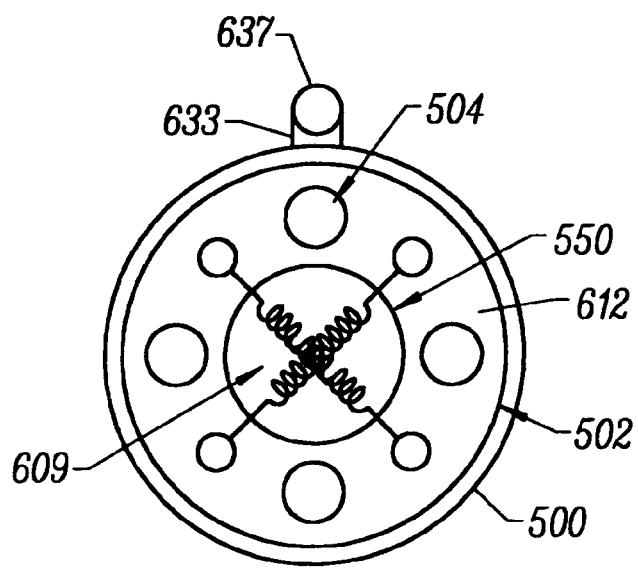
FIGS. 11–13 illustrate alternative probes according to the present invention, incorporating aspiration electrodes.
Figure 12:
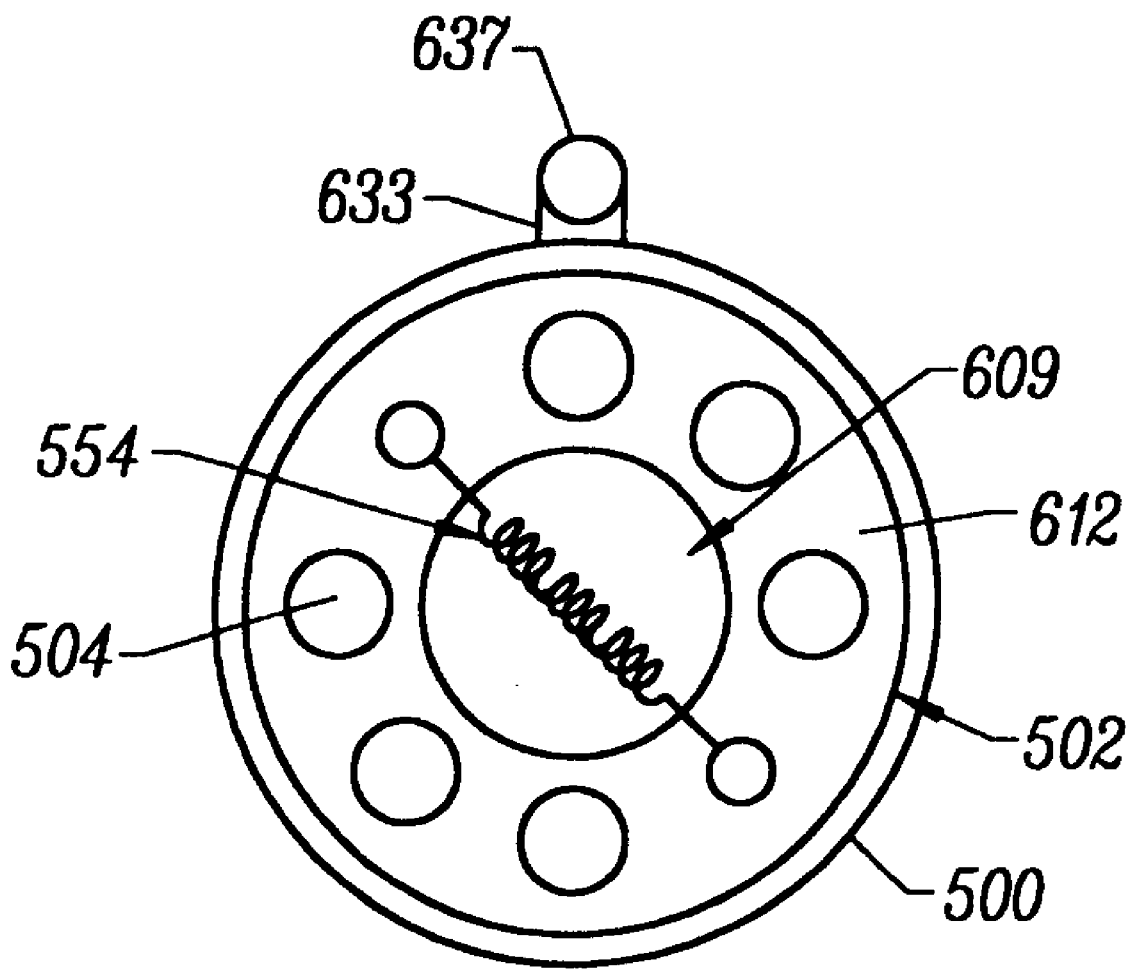
Figure 13:
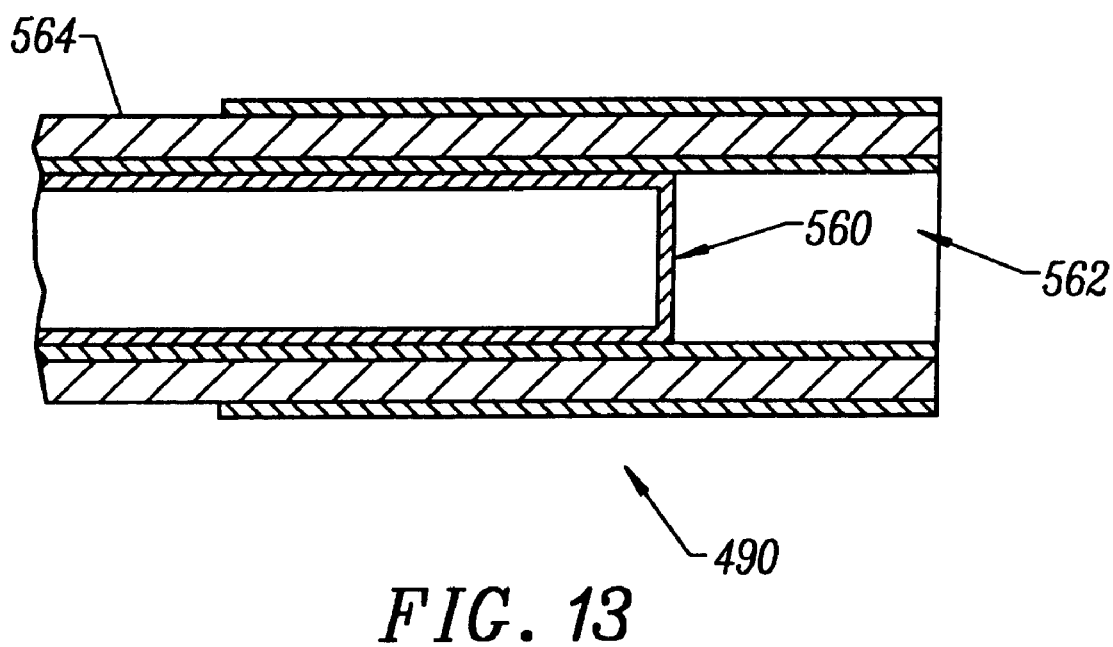

Referring now to FIGS. 11 and 12, alternative embodiments for aspiration electrodes will now be described. As shown in FIG. 11, the aspiration electrodes may comprise a pair of coiled electrodes 550 that extend across distal opening 609 of the suction lumen. The larger surface area of the coiled electrodes 550 usually increases the effectiveness of the electrodes 550 on tissue fragments passing through opening 609. In FIG. 12, the aspiration electrode comprises a single coiled electrode 552 passing across the distal opening 609 of suction lumen. This single electrode 552 may be sufficient to inhibit clogging of the suction lumen. Alternatively, the aspiration electrodes may be positioned within the suction lumen proximal to the distal opening 609. Preferably, these electrodes are close to opening 609 so that tissue does not clog the opening 609 before it reaches electrodes 554. In this embodiment, a separate return electrode 556 may be provided within the suction lumen to confine the electric currents therein.

Referring to FIG. 13, another embodiment of the present invention incorporates an aspiration electrode 560 within the aspiration lumen 562 of the probe. As shown, the electrode 560 is positioned just proximal of distal opening 609 so that the tissue fragments are ablated as they enter lumen 562. In the representation embodiment, the aspiration electrode 560 comprises a loop electrode that stretches across the aspiration lumen 562. However, it will be recognized that many other configurations are possible. In this embodiment, the return electrode 564 is located outside of the probe as in the previously embodiments. Alternatively, the return electrode(s) may be located within the aspiration lumen 562 with the aspiration electrode 560. For example, the inner insulating coating 563 may be exposed at portions within the lumen 562 to provide a conductive path between this exposed portion of return electrode 564 and the aspiration electrode 560. The latter embodiment has the advantage of confining the electric currents to within the aspiration lumen. In addition, in dry fields in which the conductive fluid is delivered to the target site, it is usually easier to maintain a conductive fluid path between the active and return electrodes in the latter embodiment because the conductive fluid is aspirated through the aspiration lumen 562 along with the tissue fragments.

FIGS. 14–17 illustrate a method for treating nasal or sinus blockages, e.g., chronic sinusitis, according to the present invention. In these procedures, the polyps, turbinates or other sinus tissue may be ablated or reduced (e.g., by tissue contraction) to clear the blockage and/or enlarge the sinus cavity to reestablish normal sinus function. For example, in chronic rhinitis, which is a collective term for chronic irritation or inflammation of the nasal mucosa with hypertrophy of the nasal mucosa, the inferior turbinate may be reduced by ablation or contraction. Alternatively, a turbinectomy or mucotomy may be performed by removing a strip of tissue from the lower edge of the inferior turbinate to reduce the volume of the turbinate. For treating nasal polypi, which comprises benign pedicled or sessile masses of nasal or sinus mucosa caused by inflammation, the nasal polypi may be contracted or shrunk, or ablated by the method of the present invention. For treating severe sinusitis, a frontal sinus operation may be performed to introduce the electrosurgical probe to the site of blockage. The present invention may also be used to treat diseases of the septum, e.g., ablating or resecting portions of the septum for removal, straightening or reimplantation of the septum.

The present invention is particularly useful in functional endoscopic sinus surgery (FESS) in the treatment of sinus disease. In contrast to prior art microdebriders, the electrosurgical probe of the present invention effects hemostasis of severed blood vessels, and allows the surgeon to precisely remove tissue with minimal or no damage to surrounding tissue, bone, cartilage or nerves. By way of example and not limitation, the present invention may be used for the following procedures: (1) uncinectomy or medial displacement or removal of portions of the middle turbinate; (2) maxillary, sphenoid or ethmoid sinusotomies or enlargement of the natural ostium of the maxillary, sphenoid, or ethmoid sinuses, respectively; (3) frontal recess dissections, in which polypoid or granulation tissue are removed; (4) polypectomies, wherein polypoid tissue is removed in the case of severe nasal polyposis; (5) concha bullosa resections or the thinning of polypoid middle turbinate; (6) septoplasty; and the like.

Figure 14:
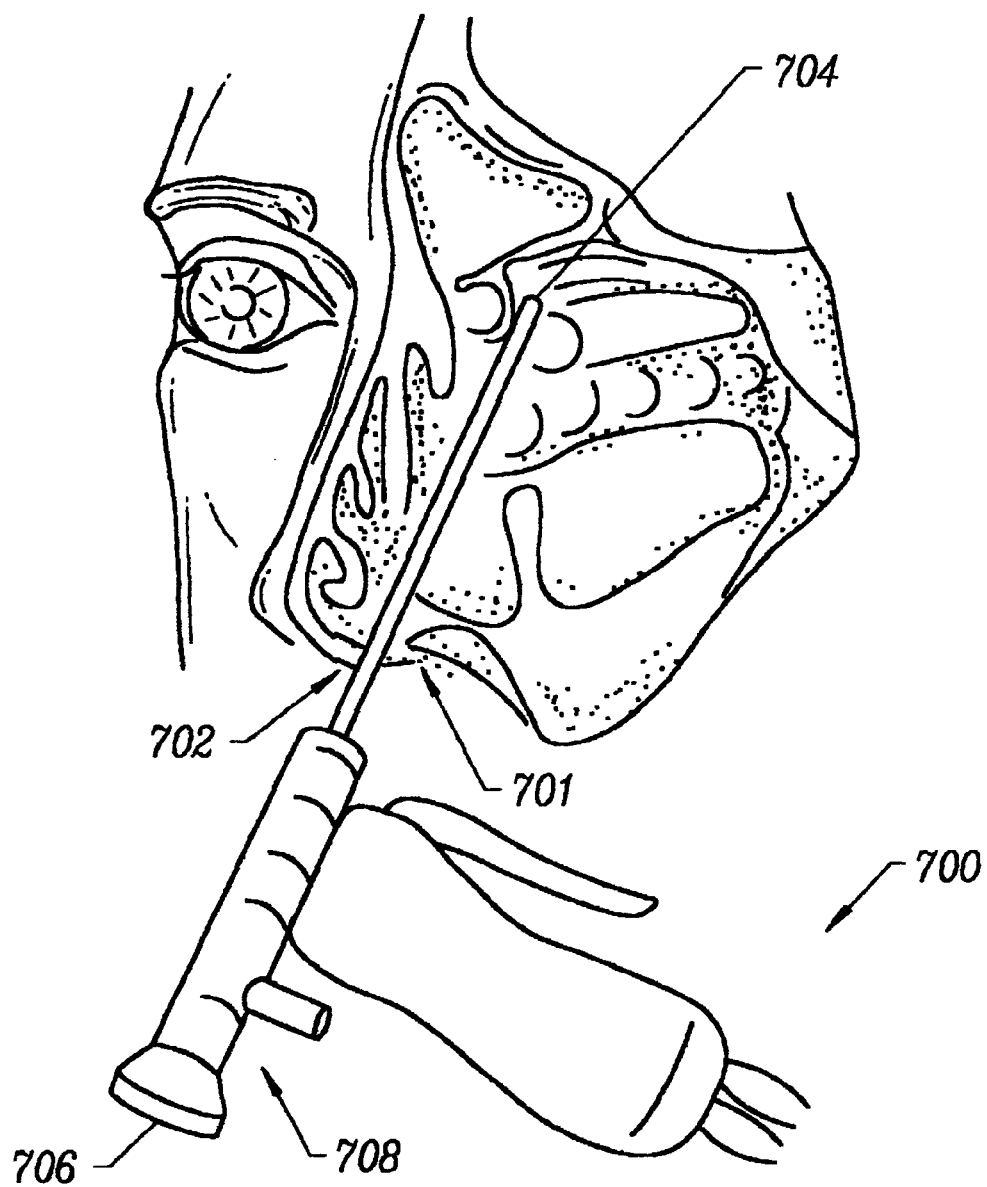
FIG. 14 illustrates an endoscopic sinus surgery procedure, wherein an endoscope is delivered through a nasal passage to view a surgical site within the nasal cavity of the patient.

FIGS. 14–17 schematically illustrate an endoscopic sinus surgery (FESS) procedure according to the present invention. As shown in FIG. 14, an endoscope 700 is first introduced through one of the nasal passages 701 to allow the surgeon to view the target site, e.g., the sinus cavities. As shown, the endoscope 700 will usually comprise a thin metal tube 702 with a lens (not shown) at the distal end 704, and an eyepiece 706 at the proximal end 708. As shown in FIG. 8, the probe shaft 500 has a bend 501 to facilitate use of both the endoscope and the probe 490 in the same nasal passage (i.e., the handles of the two instruments do not interfere with each other in this embodiment). Alternatively, the endoscope may be introduced transorally through the inferior soft palate to view the nasopharynx. Suitable nasal endoscopes for use with the present invention are described in U.S. Pat. Nos. 4,517,962, 4,844,052, 4,881,523 and 5,167,220, the complete disclosures of which are incorporated herein by reference for all purposes.

Alternatively, the endoscope 700 may include a sheath (not shown) having an inner lumen for receiving the electrosurgical probe shaft 500. In this embodiment, the shaft 500 will extend through the inner lumen to a distal opening in the endoscope. The shaft will include suitable proximal controls for manipulation of its distal end during the surgical procedure.

Figure 15:
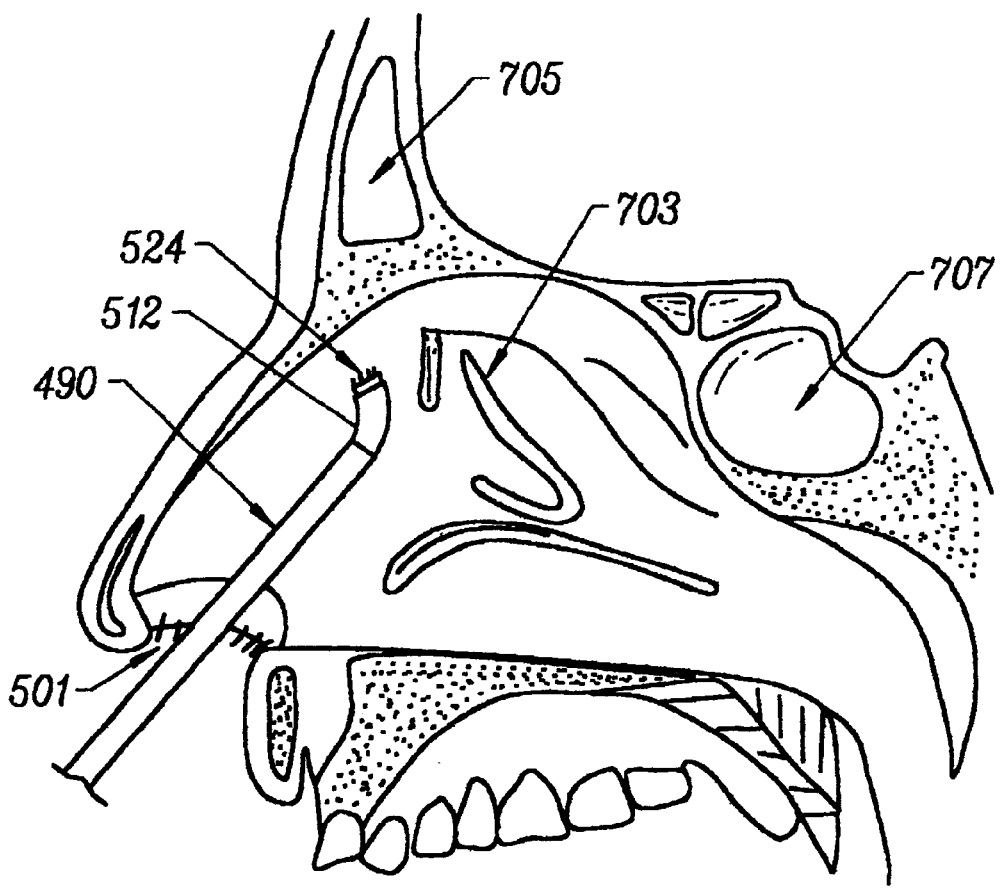
FIG. 15 illustrates an endoscopic sinus surgery procedure with one of the probes described above according to the present invention.

As shown in FIG. 15, the distal end of probe 490 is introduced through nasal passage 701 into the nasal cavity 703 (endoscope 700 is not shown in FIG. 12). Depending on the location of the blockage, the electrode terminals 504 will be positioned adjacent the blockage in the nasal cavity 703, or in one of the paranasal sinuses 705, 707. Note that only the frontal sinus 705 and the sphenoidal sinus 707 are shown in FIG. 12, but the procedure is also applicable to the ethmoidal and maxillary sinuses. Once the surgeon has reached the point of major blockage, electrically conductive fluid is delivered through tube 633 and opening 637 to the tissue (see FIG. 8). The fluid flows past the return electrode 512 to the electrode terminals 504 at the distal end of the shaft. The rate of fluid flow is controlled with valve 417 (FIG. 8) such that the zone between the tissue and electrode support 502 is constantly immersed in the fluid. The power supply 428 is then turned on and adjusted such that a high frequency voltage difference is applied between electrode terminals 504 and return electrode 512. The electrically conductive fluid provides the conduction path (see current flux lines) between electrode terminals 504 and the return electrode 512.

Figure 16A:
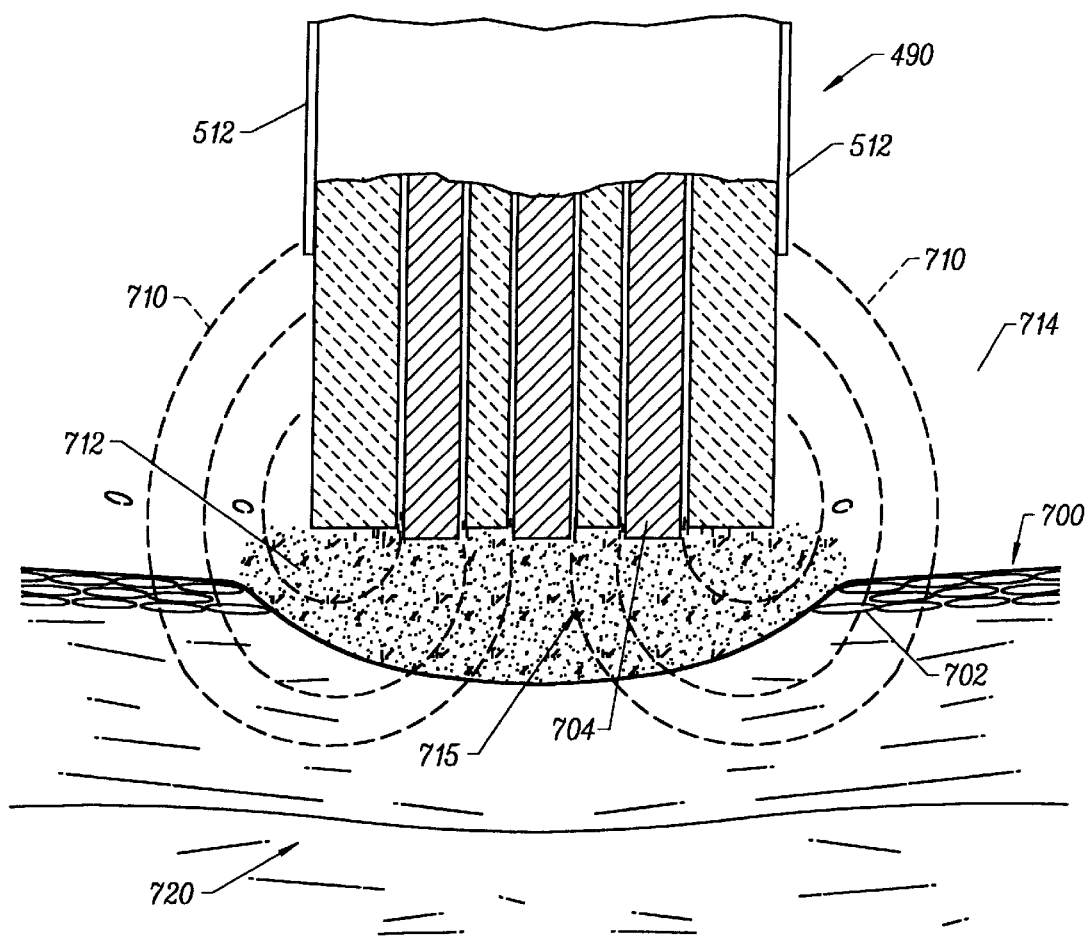
FIGS. 16A and 16B illustrate a detailed view of the sinus surgery procedure, illustrating ablation of tissue according to the present invention.
Figure 16B:
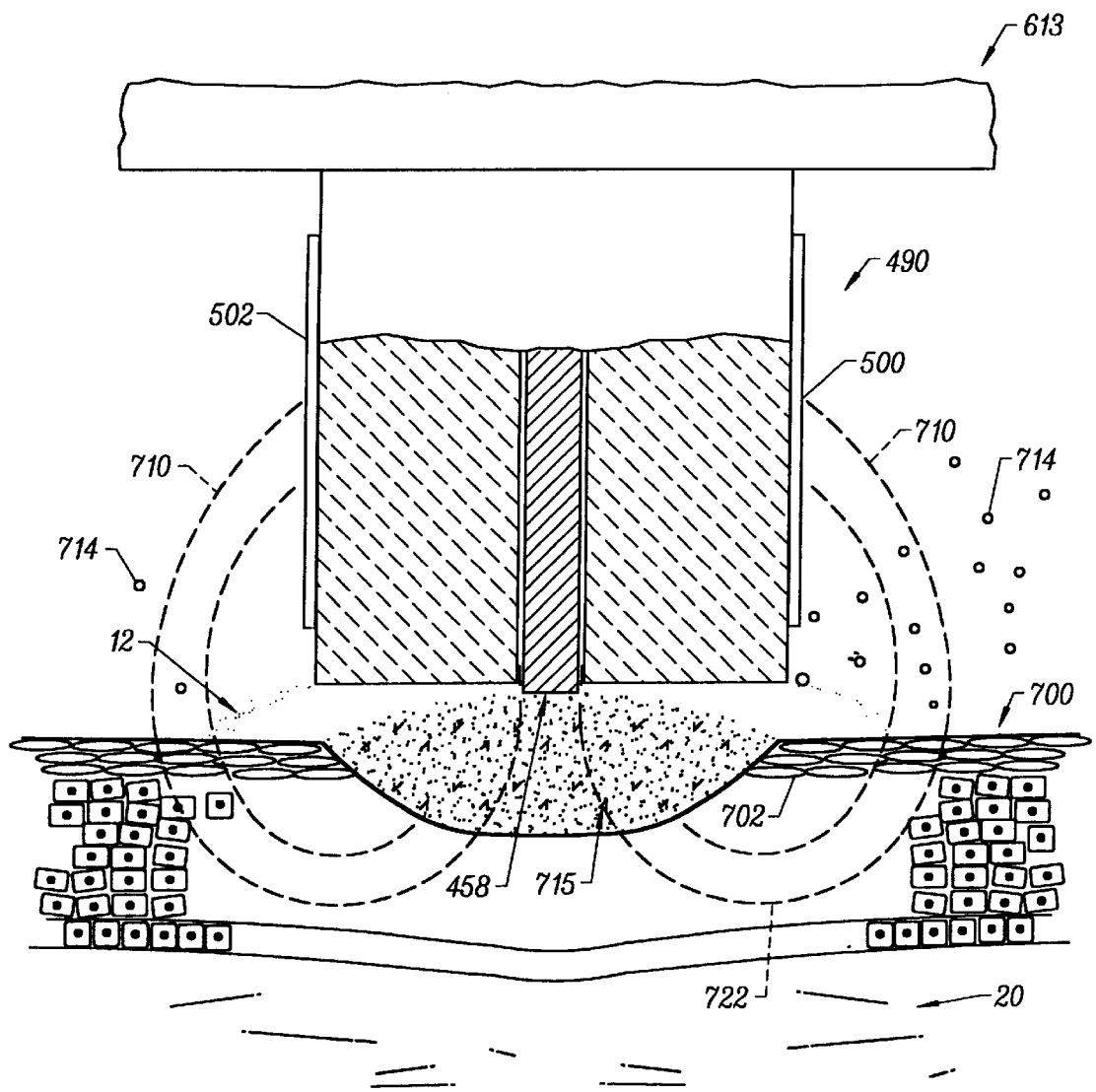

FIGS. 16A and 16B illustrate the removal of sinus tissue in more detail As shown, the high frequency voltage is sufficient to convert the electrically conductive fluid (not shown) between the target tissue 702 and electrode terminal (s) 504 into an ionized vapor layer 712 or plasma. As a result of the applied voltage difference between electrode terminal (s) 504 (or electrode terminal 458) and the target tissue 702 (i.e., the voltage gradient across the plasma layer 712), charged particles 715 in the plasma (viz., electrons) are accelerated towards the tissue. At sufficiently high voltage differences, these charged particles 715 gain sufficient energy to cause dissociation of the molecular bonds within tissue structures. This molecular dissociation is accompanied by the volumetric removal (i.e, ablative sublimation) of tissue and the production of low molecular weight gases 714, such as oxygen, nitrogen, carbon dioxide, hydrogen and methane. The short range of the accelerated charged particles 715 within the tissue confines the molecular dissociation process to the surface layer to minimize damage and necrosis to the underlying tissue 720.

During the process, the gases 714 will be aspirated through opening 609 and suction tube 611 to a vacuum source. In addition, excess electrically conductive fluid, and other fluids (e.g., blood) will be aspirated from the target site 700 to facilitate the surgeon's view. During ablation of the tissue, the residual heat generated by the current flux lines (typically less than 150° C.), will usually be sufficient to coagulate any severed blood vessels at the site. If not, the surgeon may switch the power supply 428 into the coagulation mode by lowering the voltage to a level below the threshold for fluid vaporization, as discussed above. This simultaneous hemostasis results in less bleeding and facilitates the surgeon's ability to perform the procedure. Once the blockage has been removed, aeration and drainage are reestablished to allow the sinuses to heal and return to their normal function.

Another advantage of the present invention is the ability to precisely ablate layers of sinus tissue without causing necrosis or thermal damage to the underlying and surrounding tissues, nerves (e.g., the optic nerve) or bone. In addition, the voltage can be controlled so that the energy directed to the target site is insufficient to ablate bone or adipose tissue (which generally has a higher impedance than the target sinus tissue). In this manner, the surgeon can literally clean the tissue off the bone, without ablating or otherwise effecting significant damage to the bone.

Figure 17:
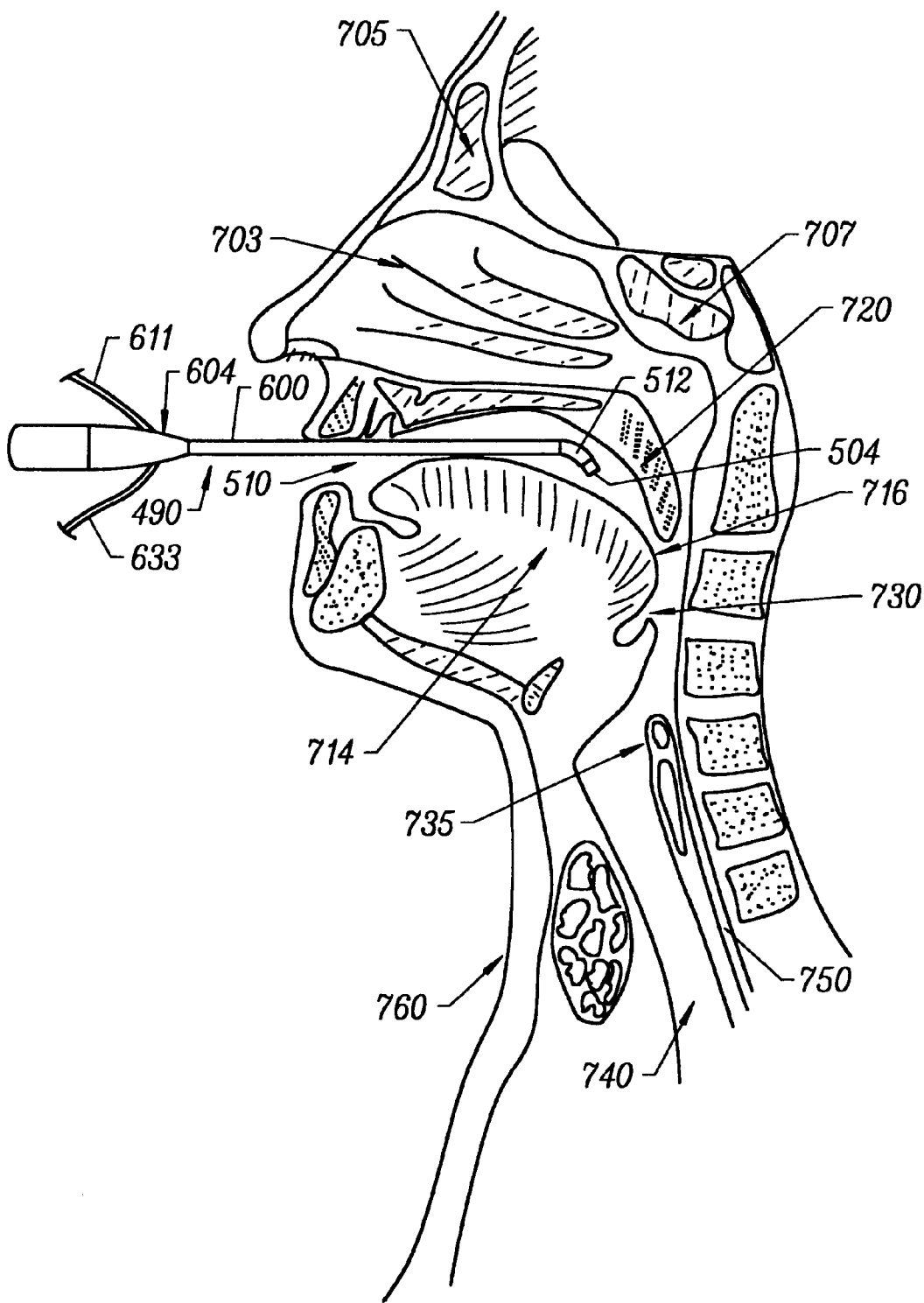
FIG. 17 illustrates a procedure for treating obstructive sleep disorders, such as sleep apnea, according to the present invention.

Methods for treating air passage disorders according to the present invention will now be described. In these embodiments, an electrosurgical probe such as one described above can be used to ablate targeted masses including, but not limited to, the tongue, tonsils, turbinates, soft palate tissues (e.g., the uvula), hard tissue and mucosal tissue. In one embodiment, selected portions of the tongue 714 are removed to treat sleep apnea. In this method, the distal end of an electrosurgical probe 490 is introduced into the patient's mouth 710, as shown in FIG. 17. An endoscope (not shown), or other type of viewing device, may also be introduced, or partially introduced, into the mouth 710 to allow the surgeon to view the procedure (the viewing device may be integral with, or separate from, the electrosurgical probe). The electrode terminals 104 are positioned adjacent to or against the back surface 716 of the tongue 714, and electrically conductive fluid is delivered to the target site, as described above. The power supply 428 is then activated to remove selected portions of the back of the tongue 714, as described above, without damaging sensitive structures, such as nerves, and the bottom portion of the tongue 714.

In another embodiment, the electrosurgical probe of the present invention can be used to ablate and/or contract soft palate tissue to treat snoring disorders. In particular, the probe is used to ablate or shrink sections of the uvula 720 without causing unwanted tissue damage under and around the selected sections of tissue. For tissue contraction, a sufficient voltage difference is applied between the electrode terminals 504 and the return electrode 512 to elevate the uvula tissue temperature from normal body temperatures (e.g., 37° C.) to temperatures in the range of 45° C. to 90° C., preferably in the range from 60° C. to 70° C. This temperature elevation causes contraction of the collagen connective fibers within the uvula tissue.

In addition to the above procedures, the system and method of the present invention may be used for treating a variety of disorders in the mouth 710, pharynx 730, larynx 735, hypopharynx, trachea 740, esophagus 750 and the neck 760. For example, tonsillar hyperplasis or other tonsil disorders may be treated with a tonsillectomy by partially ablating the lymphoepithelial tissue. This procedure is usually carried out under intubation anesthesia with the head extended. An incision is made in the anterior faucial pillar, and the connective tissue layer between the tonsillar parenchyma and the pharyngeal constrictor muscles is demonstrated. The incision may be made with conventional scalpels, or with the electrosurgical probe of the present invention. The tonsil is then freed by ablating through the upper pole to the base of the tongue, preserving the faucial pillars.

The probe ablates the tissue, while providing simultaneous hemostasis of severed blood vessels in the region. Similarly, adenoid hyperplasis, or nasal obstruction leading to mouth breathing difficulty, can be treated in an adenoidectomy by separating (e.g., resecting or ablating) the adenoid from the base of the nasopharynx.

Other pharyngeal disorders can be treated according to the present invention. For example, hypopharyngeal diverticulum involves small pouches that form within the esophagus immediately above the esophageal opening. The sac of the pouch may be removed endoscopically according to the present invention by introducing a rigid esophagoscope, and isolating the sac of the pouch. The cricopharyngeus muscle is then divided, and the pouch is ablated according to the present invention. Tumors within the mouth and pharynx, such as hemangionmas, lymphangiomas, papillomas, lingual thyroid tumors, or malignant tumors, may also be removed according to the present invention.

Other procedures of the present invention include removal of vocal cord polyps and lesions and partial or total laryngectomies. In the latter procedure, the entire larynx is removed from the base of the tongue to the trachea, if necessary with removal of parts of the tongue, the pharynx, the trachea and the thyroid gland.

Tracheal stenosis may also be treated according to the present invention. Acute and chronic stenoses within the wall of the trachea may cause coughing, cyanosis and choking.

The system and method of the present invention may also be useful to efficaciously ablate (i.e., disintegrate) cancer cells and tissue containing cancer cells, such as cancer on the surface of the epidermis, eye, colon, bladder, cervix, uterus and the like. The present invention's ability to completely disintegrate the target tissue can be advantageous in this application because simply vaporizing and fragmenting cancerous tissue may lead to spreading of viable cancer cells (i.e., seeding) to other portions of the patient's body or to the surgical team in close proximity to the target tissue. In addition, the cancerous tissue can be removed to a precise depth while minimizing necrosis of the underlying tissue.

Other modifications and variations can be made to disclose embodiments without departing from the subject invention as defined in the following claims. For example, it should be noted that the invention is not limited to an electrode array comprising a plurality of electrode terminals. The invention could utilize a plurality of return electrodes, e.g., in a bipolar array or the like. In addition, depending on other conditions, such as the peak-to-peak voltage, electrode diameter, etc., a single electrode terminal may be sufficient to contract collagen tissue, ablate tissue, or the like.

In addition, the active and return electrodes may both be located on a distal tissue treatment surface adjacent to each other. The active and return electrodes may be located in active/return electrode pairs, or one or more return electrodes may be located on the distal tip together with a plurality of electrically isolated electrode terminals. The proximal return electrode may or may not be employed in these embodiments. For example, if it is desired to maintain the current flux lines around the distal tip of the probe, the proximal return electrode will not be desired.

What is claimed is:

1. A method for treating tissue at a target site comprising:
   introducing a distal end of an instrument to a target site on or within a patient's body, wherein the instrument comprises an active electrode and a return electrode;
   positioning the return electrode at the target site such that the return electrode does not contact tissue;
   aspirating tissue from the target site through an aspiration lumen within the instrument; and
   applying high frequency voltage between the return electrode and the active electrode, the high frequency voltage being sufficient to remove at least a portion of the tissue.

2. The method of claim 1 further comprising applying high frequency voltage to an aspiration electrode coupled to the aspiration lumen, wherein the lumen has a distal opening and the aspiration electrode is positioned adjacent the distal opening.

3. The method of claim 2 wherein the aspiration electrode is positioned across the distal opening of the aspiration lumen.

4. The method of claim 2 wherein the aspiration electrode is positioned within the lumen proximal to the distal opening of the aspiration lumen.

5. The method of claim 2 wherein the aspiration and active electrodes are different electrodes, the method further comprising applying high frequency voltage between the active and return electrodes to remove at least a portion of the tissue and applying high frequency voltage between the aspiration and return electrodes to inhibit clogging of the aspiration lumen.

6. The method of claim 2 wherein the aspiration and active electrodes are the same electrode, the method further comprising applying high frequency voltage between the active and return electrodes to remove at least a portion of the tissue and applying high frequency voltage between the aspiration and return electrodes to inhibit clogging of the aspiration lumen.

7. The method of claim 2 further comprising delivering an electrically conductive fluid past the return electrode to generate a current flow path between the return electrode and the aspiration electrode.

8. The method of claim 2 further comprising:
   drawing the tissue towards the aspiration electrode such that the aspiration electrode is in contact with, or close proximity to, the tissue in the presence of an electrically conductive fluid.

9. The method of claim 1 further comprising:
   delivering electrically conductive fluid to the target site to substantially surround the active electrode with the electrically conductive fluid; and
   applying high frequency voltage between the active electrode and the return electrode, the high frequency voltage being sufficient to remove at least a portion of the tissue.

10. The method of claim 9 further comprising:
    generating tissue fragments during the tissue removal step;
    aspirating the tissue fragments through the lumen, wherein the aspiration lumen has a distal end and the instrument comprises an aspiration electrode adjacent the distal end of the aspiration lumen; and
    reducing the size of the tissue fragments by applying high frequency voltage between the aspiration electrode and the return electrode when the tissue fragments are adjacent the aspiration electrode.

11. The method of claim 1 wherein the tissue comprises a blockage within the nasal cavity or a paranasal sinus of the patient.

12. The method of claim 11 wherein the blockage is selected from the group comprising swollen tissue, turbinates, polyps, neoplasms and swollen mucus membranes lining an inner surface of the nasal cavity.

13. The method of claim 1 wherein the aspiration lumen has a distal end and the applying high frequency voltage step comprises applying high frequency voltage to a single, active electrode at the distal end of the aspiration lumen.

14. The method of claim 1 wherein the aspiration lumen has a distal end and the applying high frequency voltage step comprises applying high frequency voltage to a plurality of electrically isolated electrodes at the distal end of the aspiration lumen.

15. The method of claim 1 further comprising applying sufficient voltage to the active electrode in the presence of electrically conducting fluid to vaporize at least a portion of the fluid between the active electrode and the tissue.

16. The method of claim 15 further comprising accelerating charged particles from the vaporized fluid to the tissue to cause dissociation of the molecular bonds within the tissue structures.

* * * * *